United States Patent
Brennan et al.

(10) Patent No.: US 8,313,515 B2
(45) Date of Patent: Nov. 20, 2012

(54) MULTI-LEVEL SPINAL STABILIZATION SYSTEM

(75) Inventors: Terrence Brennan, Rocky Hill, CT (US); George F. Malcolmson, New Haven, CT (US); Carmen Walters, Hamden, CT (US); Stephen W. Zlock, Redding, CT (US); Jens Peter Timm, West Haven, CT (US)

(73) Assignee: Rachiotek, LLC, Cambridge, MA (US)

( * ) Notice: Subject to any disclaimer, the term of this patent is extended or adjusted under 35 U.S.C. 154(b) by 886 days.

(21) Appl. No.: 11/818,720

(22) Filed: Jun. 15, 2007

(65) Prior Publication Data

US 2008/0312692 A1 Dec. 18, 2008

(51) Int. Cl.
*A61B 17/70* (2006.01)

(52) U.S. Cl. ........................................ 606/256; 606/260

(58) Field of Classification Search .................... 606/60, 606/246, 250–279; 403/76, 77, 398
See application file for complete search history.

(56) References Cited

U.S. PATENT DOCUMENTS

| | | | |
|---|---|---|---|
| 3,433,510 A * | 3/1969 | Hulterstrum | 403/77 |
| 4,763,644 A | 8/1988 | Webb | |
| 5,375,823 A | 12/1994 | Navas | |
| 5,498,263 A * | 3/1996 | DiNello et al. | 606/292 |
| 5,540,688 A | 7/1996 | Navas | |
| 5,562,737 A * | 10/1996 | Graf | 623/17.14 |
| 5,582,612 A * | 12/1996 | Lin | 606/250 |
| 5,591,166 A | 1/1997 | Bernhardt | |
| 5,628,740 A | 5/1997 | Mullane | |
| 5,702,389 A | 12/1997 | Taylor | |
| 5,776,135 A | 7/1998 | Errico | |
| 5,843,081 A | 12/1998 | Richardson | |
| 5,910,142 A | 6/1999 | Tatar | |
| 5,938,663 A | 8/1999 | Petreto | |
| 5,944,719 A | 8/1999 | Leban | |
| 5,951,556 A | 9/1999 | Faccioli | |
| 5,961,516 A | 10/1999 | Graf | |
| 6,063,089 A | 5/2000 | Errico | |
| 6,113,301 A * | 9/2000 | Burton | 403/122 |

(Continued)

FOREIGN PATENT DOCUMENTS

WO 2007045899 4/2007

OTHER PUBLICATIONS

PCT International Search Report dated Oct. 10, 2008.

*Primary Examiner* — Alvin Stewart
*Assistant Examiner* — Jerry Cumberledge
(74) *Attorney, Agent, or Firm* — McCarter & English, LLP

(57) ABSTRACT

Multi-level spinal stabilization devices, systems and methods are provided that include at least one multi-level connector, one elongated member with an enlarged head, at least one pedicle screw, and at least one mechanism that supports three degrees of rotational freedom relative to both the elongated member and the pedicle screw each. The mechanism may include universal joint mechanisms or ball and socket mechanisms. In the case of the ball and socket mechanisms, the enlarged head of the elongated member cooperates with a first socket member of the multi-level connector to define a dynamic junction that allows the socket member to move relative to the enlarged head of the elongated member while remaining engaged therewith.

20 Claims, 17 Drawing Sheets

U.S. PATENT DOCUMENTS

| | | | |
|---|---|---|---|
| 6,146,383 A | 11/2000 | Struder | |
| 6,200,316 B1 | 3/2001 | Zwirkoski | |
| 6,264,658 B1 | 7/2001 | Lee | |
| 6,267,765 B1 | 7/2001 | Taylor | |
| 6,273,914 B1 | 8/2001 | Papas | |
| 6,280,443 B1 | 8/2001 | Gu | |
| 6,296,644 B1 | 10/2001 | Saurat | |
| 6,432,109 B1 | 8/2002 | Letendart | |
| 6,554,831 B1 | 4/2003 | Rivard | |
| 6,554,834 B1 | 4/2003 | Crozet | |
| 6,595,992 B1 | 7/2003 | Wagner | |
| 6,626,906 B1 | 9/2003 | Young | |
| 6,682,529 B2 | 1/2004 | Stahurski | |
| 6,730,088 B2 | 5/2004 | Yeh | |
| 6,736,816 B2 | 5/2004 | Ritland | |
| 6,802,844 B2 * | 10/2004 | Ferree | 606/258 |
| 6,835,205 B2 | 12/2004 | Atkinson | |
| 6,840,940 B2 | 1/2005 | Ralph | |
| 6,849,076 B2 | 2/2005 | Blunn | |
| 6,875,211 B2 | 4/2005 | Nichols | |
| 6,932,817 B2 | 8/2005 | Baynham | |
| 6,964,666 B2 | 11/2005 | Jackson | |
| 6,966,910 B2 | 11/2005 | Ritland | |
| 6,986,771 B2 | 1/2006 | Paul | |
| 6,989,011 B2 | 1/2006 | Paul | |
| 6,991,632 B2 | 1/2006 | Ritland | |
| 7,004,943 B2 | 2/2006 | Ferrante | |
| RE39,035 E | 3/2006 | Finn | |
| 7,029,475 B2 | 4/2006 | Panjabi | |
| 7,033,358 B2 | 4/2006 | Taylor | |
| 7,051,451 B2 | 5/2006 | Augostino | |
| 7,094,236 B2 | 8/2006 | Waisman | |
| 7,104,992 B2 | 9/2006 | Bailey | |
| 7,122,036 B2 | 10/2006 | Vanacker | |
| 7,175,622 B2 | 2/2007 | Farris | |
| 7,306,603 B2 | 12/2007 | Boehm | |
| 2002/0007183 A1 * | 1/2002 | Lee et al. | 606/61 |
| 2002/0133155 A1 | 9/2002 | Ferree | 606/61 |
| 2002/0138077 A1 | 9/2002 | Ferree | |
| 2003/0045879 A1 | 3/2003 | Minfelde | |
| 2003/0055427 A1 | 3/2003 | Graf | 606/61 |
| 2003/0153912 A1 | 8/2003 | Graf | |
| 2003/0229345 A1 | 12/2003 | Stahurski | |
| 2004/0039384 A1 | 2/2004 | Boehm | |
| 2004/0049189 A1 | 3/2004 | Le Couedic | |
| 2004/0111088 A1 * | 6/2004 | Picetti et al. | 606/61 |
| 2004/0138661 A1 * | 7/2004 | Bailey | 606/61 |
| 2005/0056979 A1 * | 3/2005 | Studer et al. | 267/118 |
| 2005/0085815 A1 | 4/2005 | Harms et al. | |
| 2005/0182401 A1 * | 8/2005 | Timm et al. | 606/61 |
| 2005/0182409 A1 | 8/2005 | Callahan | |
| 2005/0192572 A1 | 9/2005 | Abdelgany et al. | 606/61 |
| 2005/0277932 A1 * | 12/2005 | Farris | 606/61 |
| 2006/0036244 A1 | 2/2006 | Spitler et al. | 606/61 |
| 2006/0058787 A1 * | 3/2006 | David | 606/61 |
| 2006/0058790 A1 | 3/2006 | Carl et al. | 606/61 |
| 2006/0079894 A1 | 4/2006 | Colleran et al. | 606/99 |
| 2006/0079895 A1 * | 4/2006 | McLeer | 606/61 |
| 2006/0079898 A1 | 4/2006 | Ainsworth et al. | 623/17.11 |
| 2006/0079899 A1 | 4/2006 | Ritland | 606/61 |
| 2006/0084984 A1 | 4/2006 | Kim | 606/61 |
| 2006/0084987 A1 | 4/2006 | Kim | 606/61 |
| 2006/0106380 A1 * | 5/2006 | Colleran et al. | 606/61 |
| 2006/0173454 A1 | 8/2006 | Spitler et al. | 606/61 |
| 2006/0195096 A1 * | 8/2006 | Lee et al. | 606/61 |
| 2006/0229609 A1 | 10/2006 | Wang | |
| 2006/0241600 A1 * | 10/2006 | Ensign et al. | 606/61 |
| 2006/0241769 A1 | 10/2006 | Gordon et al. | 623/17.13 |
| 2006/0241771 A1 | 10/2006 | Gordon et al. | 623/17.15 |
| 2006/0247635 A1 * | 11/2006 | Gordon et al. | 606/61 |
| 2006/0293657 A1 | 12/2006 | Martmann | 606/61 |
| 2007/0167946 A1 * | 7/2007 | Triplett et al. | 606/61 |
| 2007/0198014 A1 * | 8/2007 | Graf et al. | 606/61 |
| 2007/0270805 A1 * | 11/2007 | Miller et al. | 606/61 |

* cited by examiner

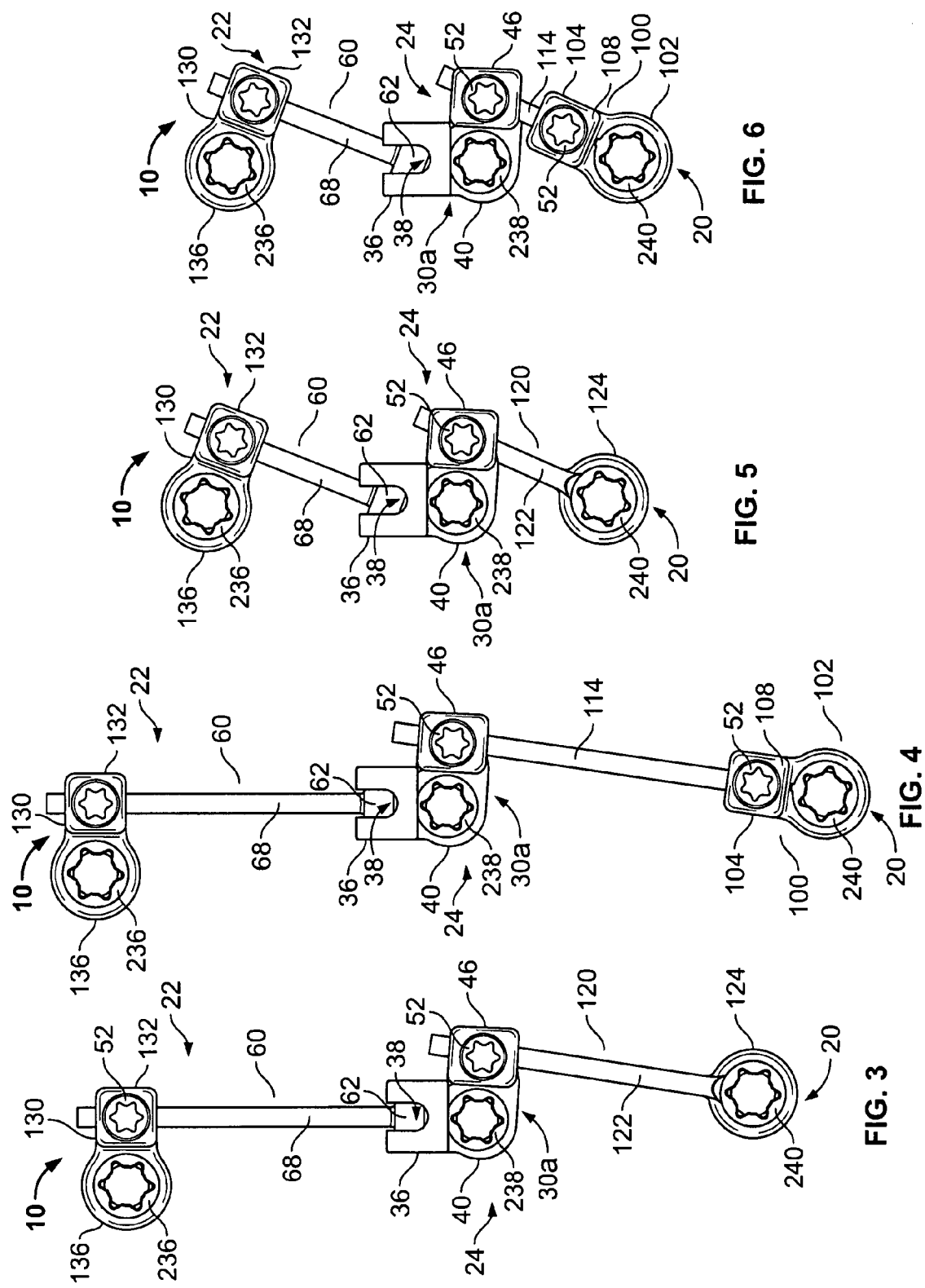

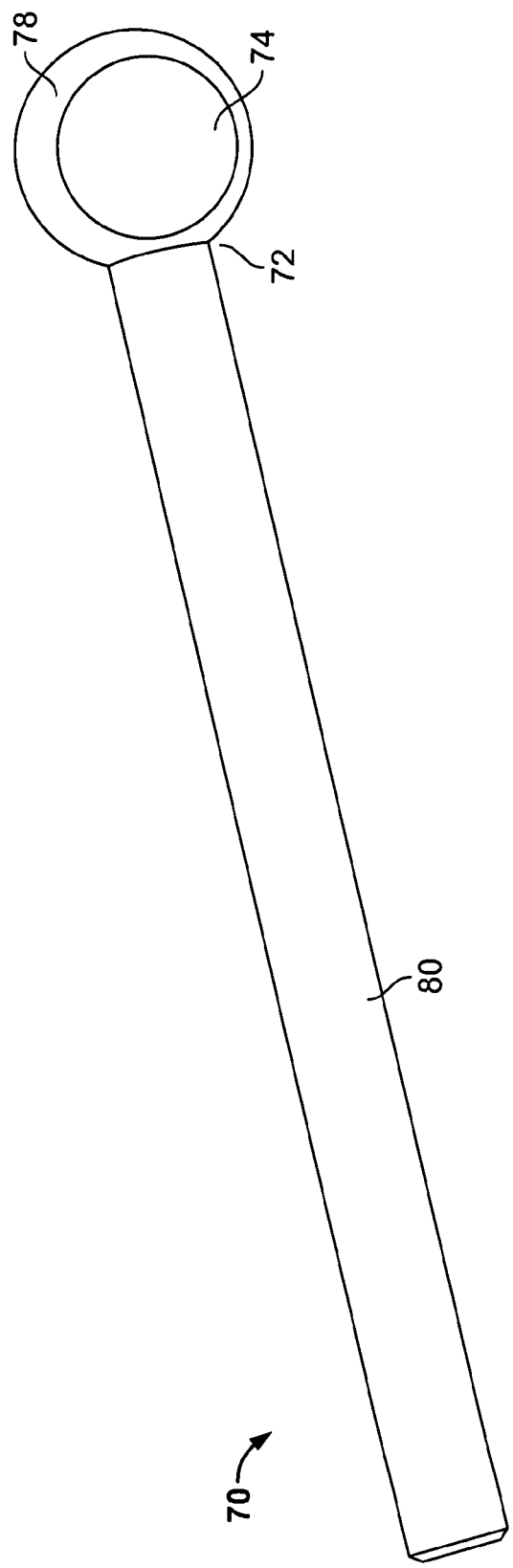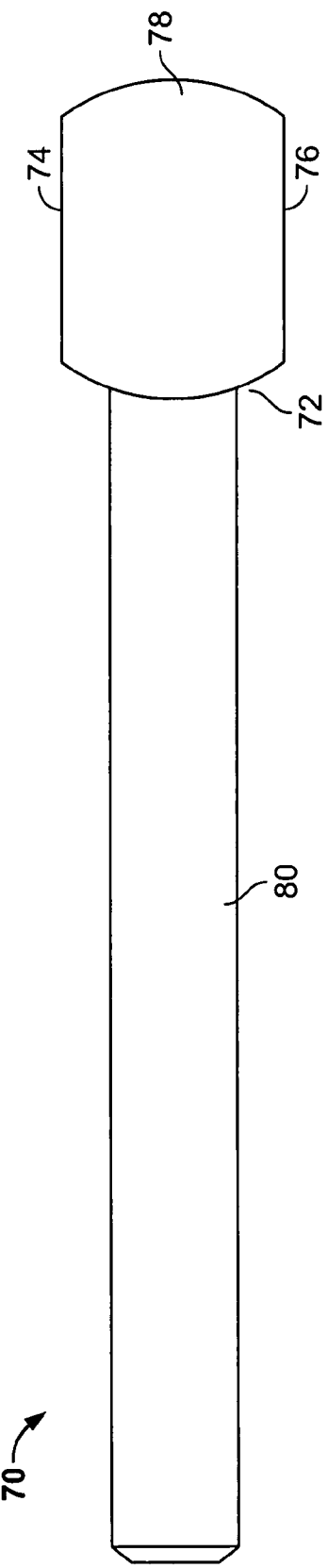
FIG. 13
FIG. 14

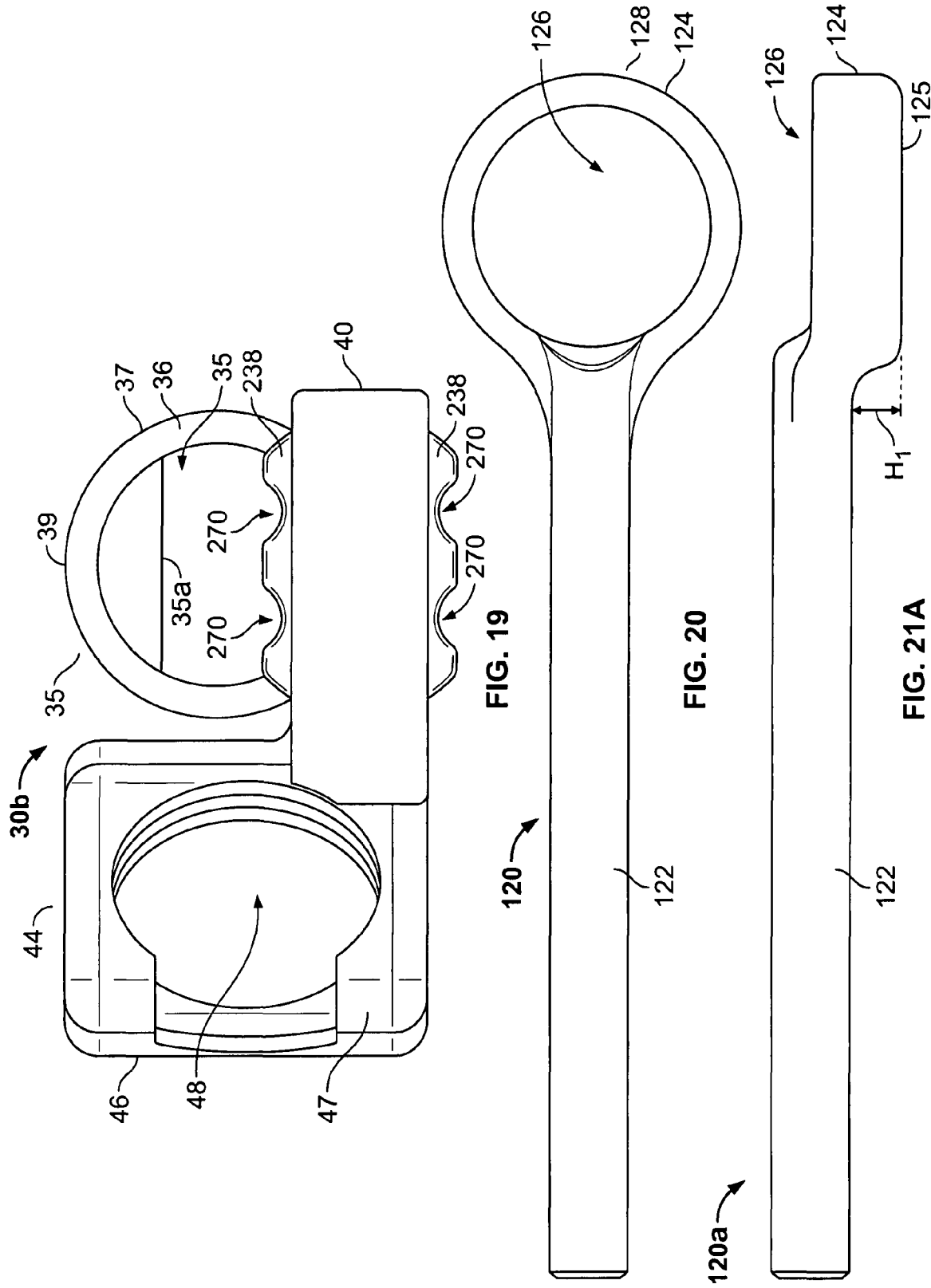

MULTI-LEVEL SPINAL STABILIZATION SYSTEM

BACKGROUND OF THE INVENTION

1. Technical Field

The present disclosure relates to advantageous methods and apparatus for spinal stabilization. More particularly, the present disclosure relates to devices, systems and methods for providing dynamic stabilization to the spine via the use of an intermediate multi-level connector for dynamic attachment of elongated members spanning one or more spinal levels at multi-level orientations.

2. Background Art

Back pain is most frequently associated with degenerative or traumatic changes in the lumbar vertebrae and/or disks. The vast majority of the 30 million U.S. patients who report back pain each year resolve their pain with conservative treatment or, simply, rest and exercise. However, approximately 15 percent, or 4.5 million, low back pain sufferers fail conservative therapy and are left with debilitating pain. Of these, some 500,000 opt for surgery.

In addition to alleviating pain, spine surgery seeks to minimize damage to adjacent supportive muscle and skeletal tissues. Spine fusion used to be the only option for patients, and remains the most common surgical procedure. However, the by-products of this surgical procedure and preparation for fusion are damage of the posterior muscles and loss of intervertebral motion which can compromise postoperative function and place abnormal stresses on the adjacent spine levels.

New treatment modalities, collectively called motion preservation devices, are currently being developed to address these limitations. Some promising therapies are in the form of nucleus, disc or facet replacements. Other motion preservation devices provide dynamic internal stabilization of the injured and/or degenerated spine, e.g., the Dynesys stabilization system (Zimmer, Inc.; Warsaw, Ind.) and the Graf Ligament. A major goal of this concept is the stabilization of the spine to prevent pain while preserving near normal spinal function. Dynamic spinal stabilization systems use non-rigid materials to stabilize the affected lumbar region, to alter the load bearing forces and stress patterns in the affected region, and to preserve the anatomy and mobility of the spine by preventing degeneration in adjacent regions.

Dynamic stabilization designs may vary according to spine level, from cervical to thoracic to lumbar to sacral. For posterior systems, screw or hook based systems are widely used and are secured to rods, plates or other forms of stabilization members. The lumbosacral junction can bear the largest loads on the spine and the highest stresses. Further, the S-1 pedicle, made up for five fused vertebrae below the lumbar region, is larger than the lumbar pedicles, having Sacral Ala or "wings", and presents unique anatomical problems in spinal stabilization methodologies.

With the foregoing in mind, those skilled in the art will understand that a need exists for spinal stabilization devices, systems and methods that preserve spinal motion, that include dynamically attached elongated members for implantation across one or more levels of the spine.

SUMMARY OF THE PRESENT DISCLOSURE

According to the present disclosure, advantageous devices, systems and methods for spinal stabilization are provided. According to preferred embodiments, the disclosed devices, systems and methods provide dynamic stabilization to the spine so as to provide clinically efficacious results. In addition, the disclosed devices, systems and methods offer clinical advantages, including ease of installation, versatility/flexibility in application, and superior clinical results for individuals encountering lower back pain and other spine-related difficulties.

According to exemplary implementations of the present disclosure, advantageous devices, devices, systems, kits for assembly, and/or methods for dynamic stabilization are provided. The disclosed devices, systems, kits and methods generally include a multi-level dynamic spinal stabilization system with elongated members, e.g., spinal support rods. The disclosed elongated members extend axially along the spine, as do spinal support rods used in connection with lumbar fusion and other related procedures.

According to exemplary embodiments of the present disclosure, each one of the elongated members includes an axial span that extends in an axial direction across a spinal level to promote efficacious spinal stabilization thereacross, and that manifests a radially segmented geometry relative to the axial direction. In some such embodiments, the elongated member is configured and dimensioned for implantation adjacent the spine such that at least two axial spans of the elongated member extend across respective spinal levels of the spine to promote efficacious spinal stabilization across both such spinal levels. In some such embodiments, the axial span has a rod-like profile and is adapted to be mounted with respect to a patient's spine using a connector at a ball and socket joint. Such rod-like profile can include a diameter in a range of from about 3.5 mm to 6.35 mm (although alternative dimensions are contemplated). In other embodiments, the axial span has a cross-like profile or other shape. Further with respect to some such exemplary embodiments, the axial span is substantially rigid as against axial forces arrayed in compression and/or tension. Yet further with respect to some such embodiments, the radially segmented geometry includes a rod of radially unitary construction and extending in the axial direction. According to further exemplary embodiments, the rod can be fabricated, in whole or in part, from a superelastic material.

In accordance with still further embodiments of the present disclosure, the elongated members may include enlarged heads at one end centered along the longitudinal axis of the rod. In one embodiment of the present disclosure, the enlarged head resembles a ball-like structure that is substantially spherical with a planar surface at a distal end. In another embodiment of the present disclosure, the ball-like structure is semi-circular in geometry with a substantially planar surface on one side and a second substantially planar surface opposite thereto, resembling a disk on a rod and similar in appearance to a conventional "lollypop". The elongated members also include a simple rod without an enlarged head.

According to exemplary embodiments of the present disclosure, the multi-level spinal stabilization system includes an intermediate connector with a first aperture and a socket that extends in an axial direction substantially along the spine for reception and dynamic fixation of the enlarged ball-like structure of a first elongated member. The enlarged ball-like head of the elongated member is not statically fixed in the socket, but retains some advantageous freedom of movement after the axial, longitudinal rod portion of the elongated member is fixed with respect to an attachment member at a second attachment connector, e.g., at the next vertebral segment, by means of an attachment member, e.g., a set screw In some such embodiments, the intermediate connector includes a second socket area, laterally positioned with respect to the first socket, which is dimensioned and configured for reception of a spherical element of a pedicle screw assembly. The intermediate connector may also includes a third aperture laterally positioned with respect to the second socket, which is dimensioned and configured for reception of an attachment member and a set screw for static fixation of the longitudinal portion of a second elongated member extending from a lower vertebral/sacral segment.

In accordance with still further embodiments of the present disclosure, the multi-level stabilization system has a first end which includes an inferior vertebral connector for interaction with the intermediate connector via an elongated member. In some such embodiments, the inferior vertebral connector is dimensioned and configured for superior placement and connection to the intermediate connector by means of an elongated member which takes the form of a rod on a ring, wherein the ring contains an aperture designed to be a socket for reception of a dynamically fixed pedicle screw assembly, and the rod extends toward the intermediate connector at an advantageously chosen orientation. In another such embodiment, the inferior vertebral connector includes a socket in a box-like housing for static fixation of the elongated member of the present disclosure by means of a set screw and an attachment member inside the socket.

In accordance with still further embodiments of the present disclosure, the multi-level stabilization system has a second end which includes a third superior connector. The third superior connector is dimensioned and configured with a socket for reception of an attachment member into which the longitudinal rod of an elongated element is secured by means of a set screw and attachment member. The third connector generally includes another socket for reception of a dynamic pedicle screw assembly.

In accordance with still further embodiments of the present disclosure, a kit for assembling a multi-level stabilization system is provided. Such kit includes elongated members, each elongated member having a rod having an axial span extending in an axial direction so as to span at least one spinal level, and including a ball-like structure at one end as well as conventional straight rods without enlarged heads. Such kit also includes a plurality of attachment devices attachable to the axial span so as to couple the spinal support rod to the spine of the patient across the spinal level, including an intermediate connector and at least one inferior attachment member. In some such embodiments, the multi-level stabilization system includes at least two pedicle screw assemblies, i.e. pedicle screw, snap ring, set screw and spherical element.

The multi-level stabilization system of the present disclosure advantageously includes one or more of the following structural and/or functional attributes:

Spine surgery patients whose conditions indicate that they would benefit from retaining at least some spinal motion in flexion, extension, lateral bending and/or axial rotation may be fitted with a multi-level stabilization device/system as disclosed herein rather than undergo procedures involving substantial immobilization as between adjacent vertebrae;

The elongated members/spinal support rods disclosed herein allow for extra rotational degrees of freedom by virtue of the enlarged, ball-like heads when used in combination with the rotating ball and socket joint of the intermediate connector.

The multi-level dynamic spinal stabilization system disclosed herein allows for superior sacral to lumbar vertebral spanning by virtue of the specially designed inferior vertebral connectors/rods and multi-angle orientation utility of the inferior vertebral connector and the intermediate connector, as well as for superior vertebral spanning across two levels.

The multi-level connectors and elongated members/spinal support rods disclosed herein are adaptable to pedicle screw, hook, plate and/or stem attachment, can be used across one or more spinal levels; permit desirable levels of spinal extension, spinal flexion, and/or spinal lateral bending as between adjacent spinal vertebrae, and allow for adjustable attachment points along their axial lengths to accommodate differing patient anatomies.

Advantageous spine stabilization devices, systems, kits for assembling such devices or systems, and methods may incorporate one or more of the foregoing structural or functional attributes. Thus, it is contemplated that a system, device, kit and/or method may utilize only one of the advantageous structures/functions set forth above, or all of the foregoing structures/functions, without departing from the spirit or scope of the present disclosure. Stated differently, each of the structures and functions described herein is believed to offer benefits, e.g., clinical advantages to clinicians or patients, whether used alone or in combination with others of the disclosed structures/functions.

Additional advantageous features and functions associated with the devices, systems, kits and methods of the present disclosure will be apparent to persons skilled in the art from the detailed description which follows, particularly when read in conjunction with the figures appended hereto. Such additional features and functions, including the structural and mechanistic characteristics associated therewith, are expressly encompassed within the scope of the present invention.

As noted above, advantageous spine stabilization devices, systems and methods may incorporate one or more of the foregoing structural and/or functional attributes. Thus, it is contemplated that a system, device and/or method may utilize only one of the advantageous structures/functions set forth above, a plurality of the advantageous structures/functions described herein, or all of the foregoing structures/functions, without departing from the spirit or scope of the present disclosure. Stated differently, each of the structures and functions described herein is believed to offer benefits, e.g., clinical advantages to clinicians and/or patients, whether used alone or in combination with others of the disclosed structures/functions.

BRIEF DESCRIPTION OF THE DRAWINGS

To assist those of ordinary skill in the art in making and using the disclosed devices and systems, reference is made to the appended figures, in which:

FIG. 3 is a top view of a multi-level spinal stabilization device/system in accordance with a first embodiment of the present disclosure;

FIG. 4 is a top view of a multi-level spinal stabilization device/system in accordance with a second embodiment of the present disclosure;

FIG. 5 is a top view of a multi-level spinal stabilization device/system in accordance with a first embodiment of the present disclosure showing an alternate rod fixation;

FIG. 6 is a top view of a multi-level spinal stabilization device/system in accordance with a second embodiment of the present disclosure showing an alternation rod fixation;

FIG. 13 is a side elevational view of an elongated member in accordance with a second embodiment of the present disclosure;

FIG. 14 is a front elevational view of an intermediate multi-level connector in accordance with a second embodiment of the present disclosure engaged with an elongated member engaged in first attachment member;

FIG. 19 is a first side elevational view of an intermediate multi-level connector in accordance with a second embodiment of the present disclosure;

FIG. 20 is a top view of a first embodiment of an inferior vertebral connector, a rod on a ring;

FIG. 21a is a side elevational view of a first embodiment of a inferior vertebral connector, a rod on a ring showing a low rod to ring offset;

DESCRIPTION OF EXEMPLARY EMBODIMENTS

The present disclosure provides advantageous devices, systems and methods for providing dynamic spinal stabilization. More particularly, the present disclosure provides a multi-level dynamic spinal stabilization system with a multi-level intermediate connector configured for attachment of an elongated member in a dynamic ball and socket junction and including a second attachment member for reception of an elongated member extending from an inferior end connector at a variable orientation with respect to other elongated members of the system.

The exemplary embodiments disclosed herein are illustrative of the advantageous spinal stabilization devices/systems and surgical implants of the present disclosure, and of methods/techniques for implementation thereof. It should be understood, however, that the disclosed embodiments are merely exemplary of the present invention, which may be embodied in various forms. Therefore, the details disclosed herein with reference to exemplary dynamic stabilization systems and associated methods/techniques of assembly and use are not to be interpreted as limiting, but merely as the basis for teaching one skilled in the art how to make and use the advantageous spinal stabilization systems and alternative surgical implants of the present disclosure.

Figure 1:
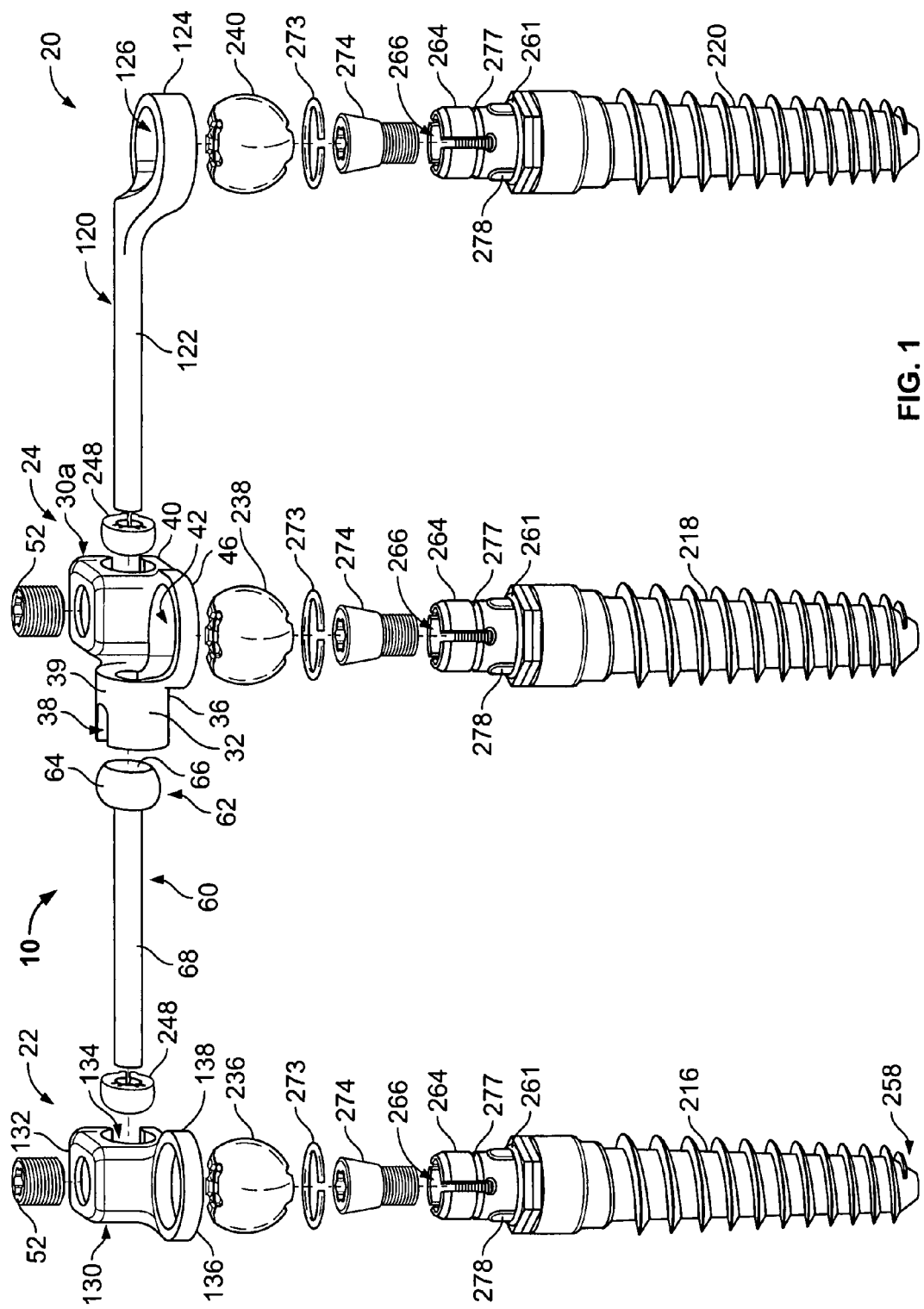
FIG. 1 is an exploded side view of a multi-level spinal stabilization device/system in accordance with a first embodiment of the present disclosure.

With reference to FIGS. 1-30, embodiments of the advantageous dynamic multi-level spinal stabilization system are shown. In a first embodiment, exemplary multi-level stabilizing system 10 defines a first inferior end 20, a second superior end 22, and a center section 24 that includes an intermediate multi-level connector 30. The schematic depiction of FIG. 1 includes three attachment members 120, 30, 130, two elongated members 60, 122, and three pedicle screws 216, 218, 220, but it is to be understood that the "first inferior end" and/or the "second superior end" and/or the "center section" may form intermediate locations, with additional pedicle screw(s) and/or stabilizing attachment member(s) positioned therebeyond or therebetween.

Figure 2:
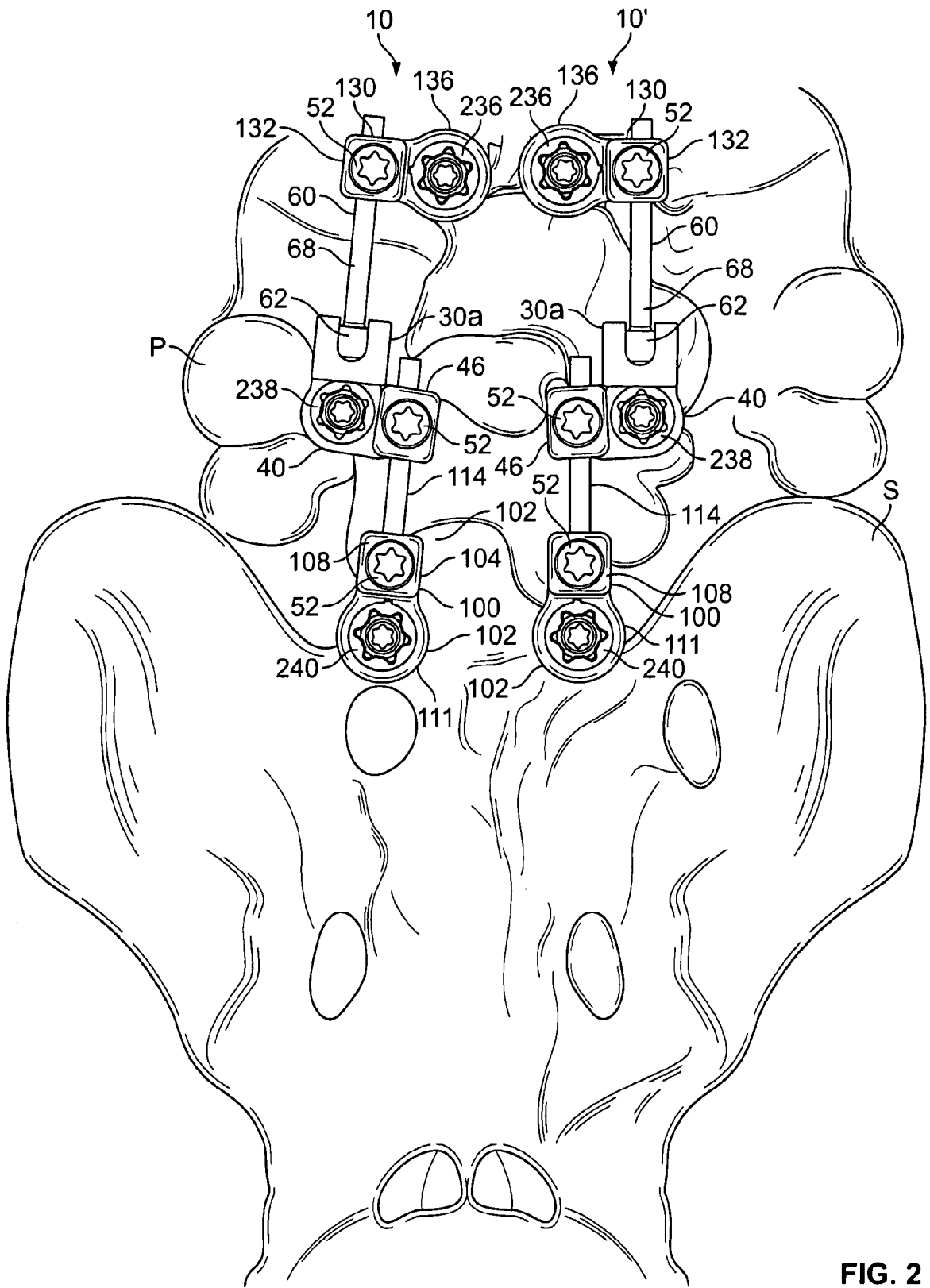
FIG. 2 is an illustrative view of a multi-level spinal stabilization device in accordance with a second embodiment of the present disclosure in situ.

Referring to FIG. 2, the multi-level stabilization system 10, 10' is depicted affixed to a spine attached by the first end 20 at the sacrum "S" and extending axially up a spine, attaching at the pedicle P of the last lumbar vertebrae at the center section 24 and even further up the spine at the second end 22. In one embodiment, the systems 10, 10' are affixed to the spine such that system 10' mirrors system 10 to accommodate a right-hand orientation. It is to be understood that the first inferior end 20 could be implanted at any lumbar vertebra and is not limited to implantation at the sacrum.

Referring to FIGS. 1-18, toward the center area 24, an intermediate multi-level connector 30a, 30b is provided that enables a multi-level spinal construct by means of sockets 34, 48 which are adapted to received/interact with two separately aligned rods 122, 60 and a socket 42 for a pedicle screw 218. The intermediate multi-level connector 30a, 30b includes a unitarily formed body 31 with two rotating ball and socket joints 35, 42 and one locking ball and socket joint 48.

Figure 7:
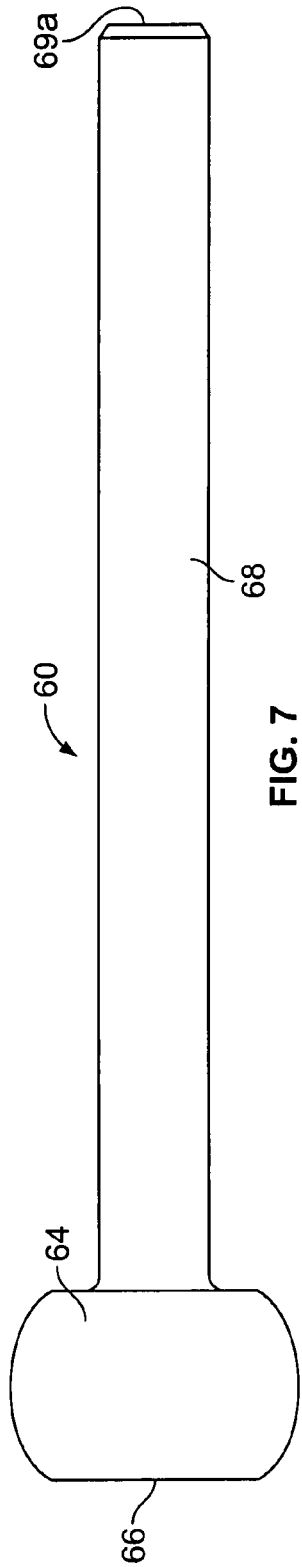
FIG. 7 is a top perspective view of an elongated member in accordance with a first embodiment of the present disclosure.
Figure 8:
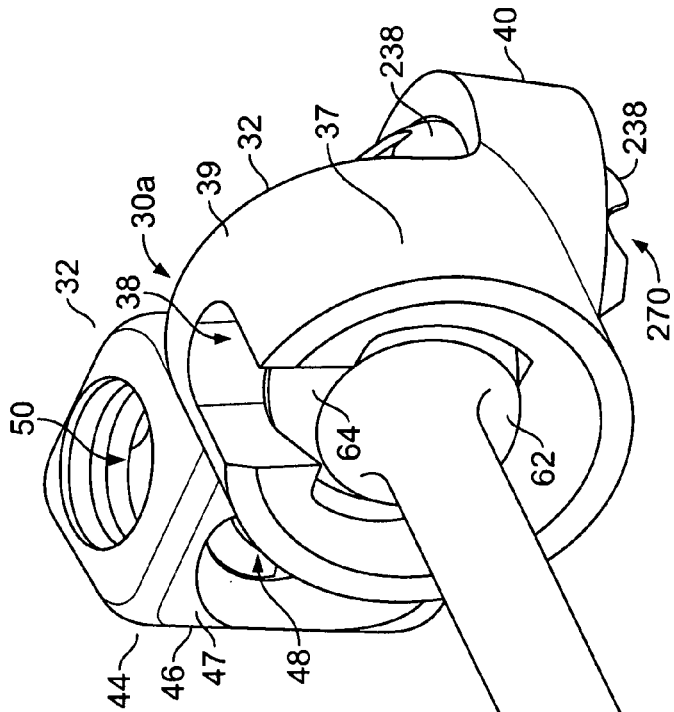
FIG. 8 is a perspective view of an intermediate multi-level connector in accordance with a first embodiment of the present disclosure with an elongated member engaged in the socket of a first attachment member.
Figure 9:
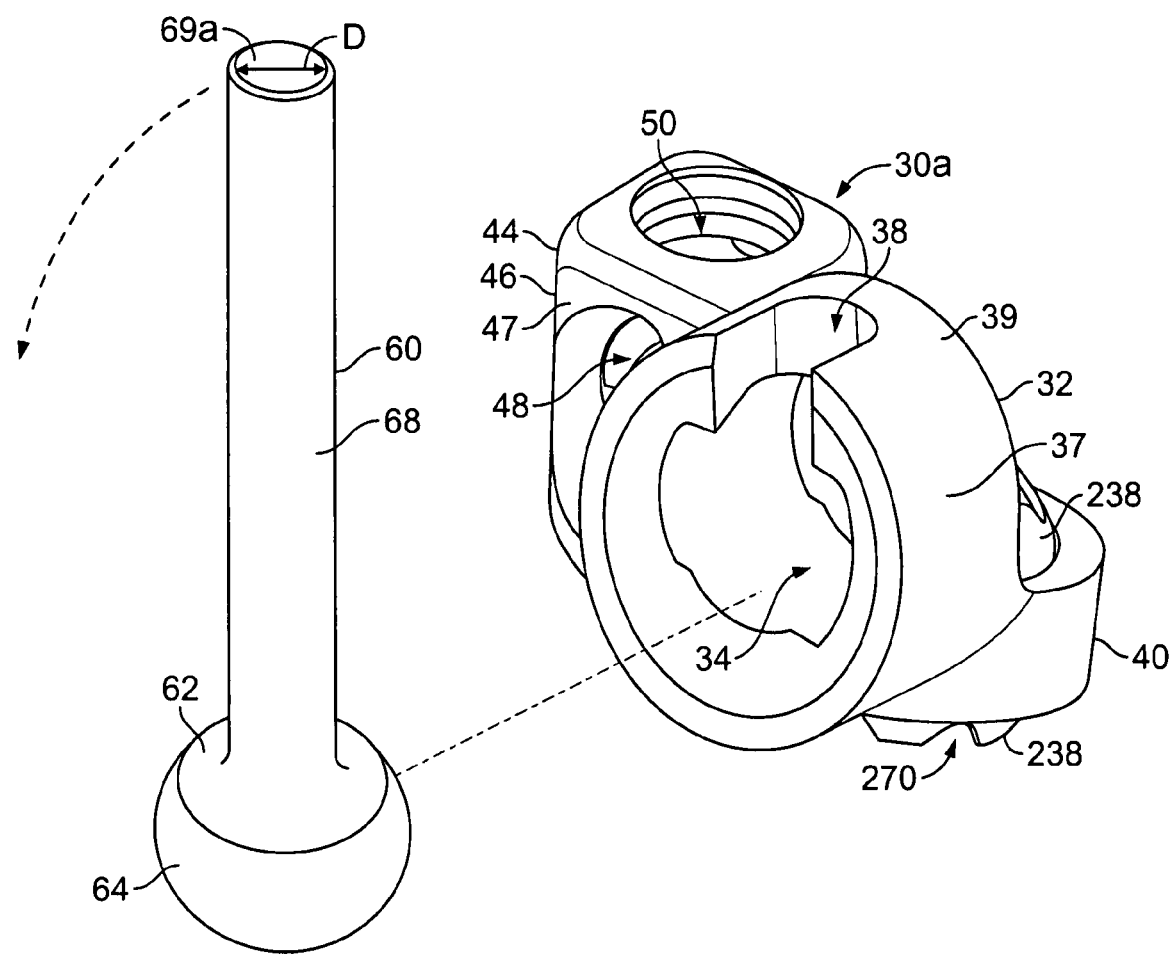
FIG. 9 is a perspective exploded view of an intermediate multi-level connector in accordance with a first embodiment of the present disclosure with an elongated member 90 degrees offset for engagement in the socket of a first attachment member.
Figure 10:
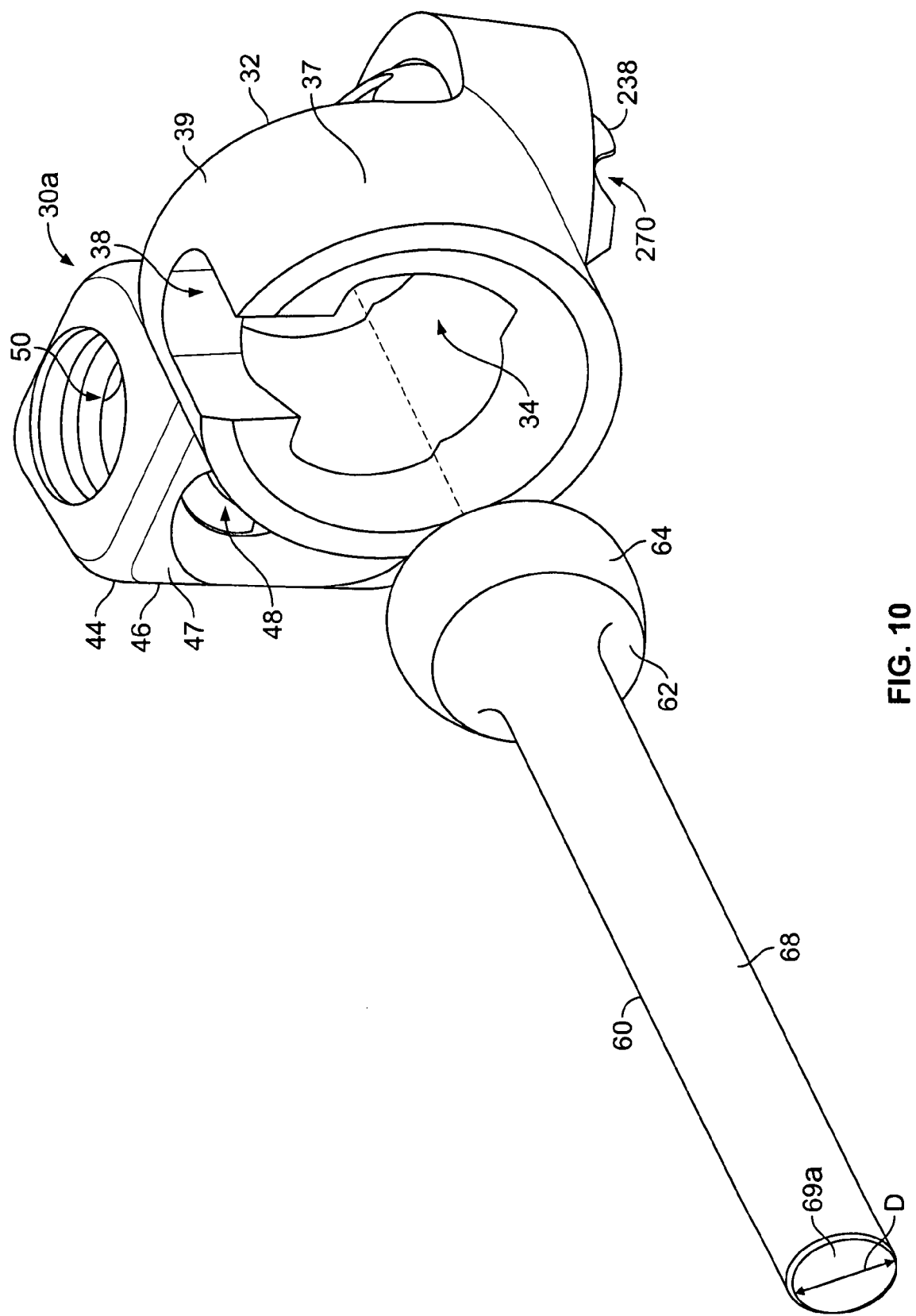
FIG. 10 is an exploded perspective view of an intermediate multi-level connector in accordance with a first embodiment of the present disclosure with an elongated member engaged in the socket of a first attachment member.
Figure 11:
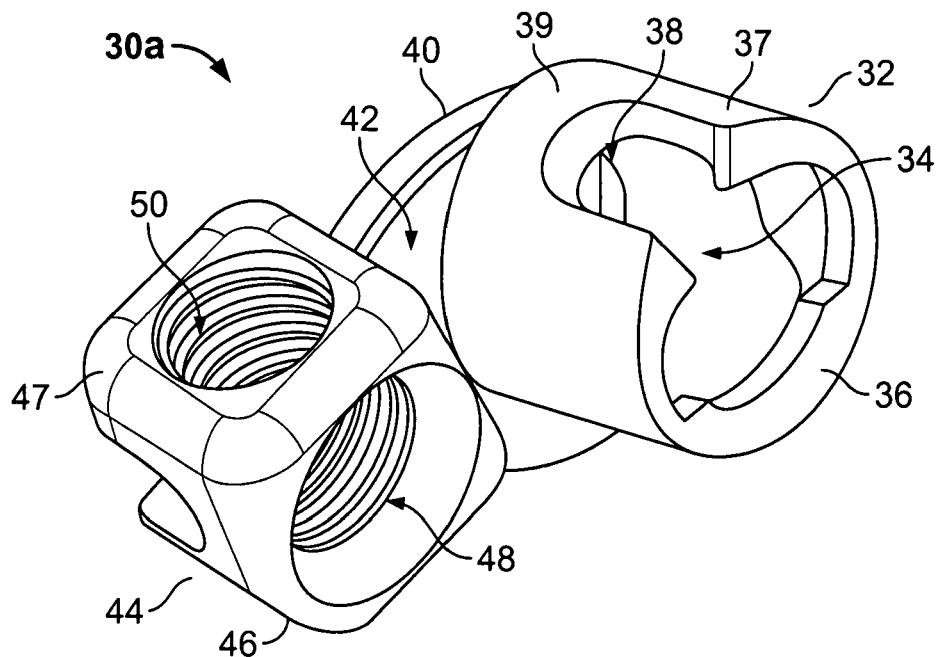
FIG. 11 is a perspective view of an intermediate multi-level connector in accordance with a first embodiment of the present disclosure.
Figure 12:
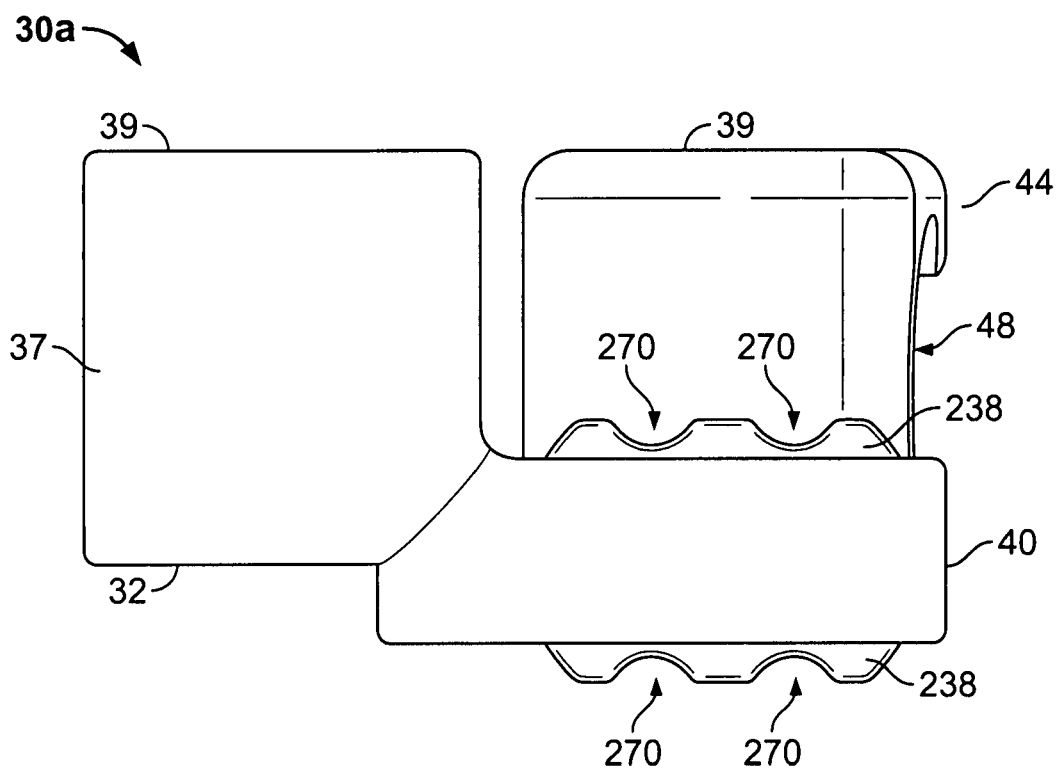
FIG. 12 is a left side elevational view of an intermediate multi-level connector in accordance with a first embodiment of the present disclosure.

In a first embodiment, the intermediate connector 30 includes first rotating ball and socket joint 35 that is dimensioned and configured to receive and fix the enlarged ball-like head 64 of an elongated member 60, as shown in FIGS. 7-12. Referring to FIG. 11, a socket 34 is formed from an annular bore of a cylindrical housing 36 such that when the enlarged head 64 of the elongated member 60 is placed in the socket 35, the rod portion 68 of the elongated member 60 will extend in an axial/longitudinal direction opposite thereto. The cylindrical housing 36 includes a substantially cylindrically shaped outer surface 37. The intermediate connector 30a, defines a cylindrical housing 36 that includes a U-shaped slot 38 at the top surface 39 that extends from the top surface 39 of the cylindrical housing 36 through to the socket 35 for assembly purposes of an elongated member 60 with an enlarged head 64 that resembles a ball as shown in FIG. 7. The exemplary elongated member 70 has a rod with an outer perimeter 69 in end view that has a substantially circular cross-section and a flat end 69a. The circular outer perimeter 69 defines a diameter "D" of rod 68 of an extent that is in a lower range typically smaller than that of conventional spinal stabilization rods (e.g., 3.5 mm to about 6.35 mm or alternative dimensions). In other embodiments, the cross-section of the elongated member is non-circular. For example, alternative cross-sectional geometries may be employed, e.g., a T-shaped or rectangular cross-section.

The elongated member 60 also includes an enlarged head 62 unitarily formed with the rod 68. In one embodiment, the enlarged head 62 has a substantially spherical surface 64 transverse to the axis of the rod 68 with a planar outer end 66 that is substantially perpendicular to the axis of the rod 68. In a general sense, this exemplary embodiment resembles a ball on a stick. Referring to FIG. 13a, the elongated member 60 is front loaded into the socket 34 of the intermediate multi-level connector 30 by sliding the rod 68 of the elongated member 60 through the U-shaped slot 38 formed in the cylindrical housing 36, then rotating the rod 68 by about 90 degrees relative to the socket. Positioning and/or introducing the elongated member 60 through the U-shaped slot 38 at a substantially perpendicular orientation to the connector 30 provides advantageous clinical usage.

Referring to FIGS. 15-19, a second exemplary embodiment of an intermediate level connector 30b includes an elongated member 70 with an axis defined by an axial/longitudinal direction along which the elongated member 70 characteristically extends. Referring to FIGS. 13-14, another embodiment includes an elongated member 70 with an enlarged head 72 that resembles a disk or a "lollypop" with planar surfaces 74, 76 opposite each other which are substantially parallel to the longitudinal axis of the rod 80. Assembly of this alternative exemplary embodiment of elongated member 70 with its correspondingly configured socket 35 in the intermediate connector 30b is effectuated by back loading the rod portion through the back of the socket 37a until the enlarged head 72 stops/abuts against the inside of the correspondingly configured socket 35. The elongated member 70 is then rotated (about 90 degrees) until the planar surfaces 74, 76 are substantially perpendicular to the inner planar surface 35a of the socket 35. The elongated member 70 is advantageously prevented from moving back out of the socket 35 when rotated 90 degrees relative to the planar surface 35a of the socket 35. The rod part 80 is fixed at the second end 22 level in a third connector 130 when a set screw 52 presses on the locking ball 248 in ball-in-a-box housing 132.

The elongated member of either embodiment 60, 70 is similar to conventional spinal stabilization rods in that it is substantially dimensionally stable in the radial direction (e.g., transversely/perpendicularly relative to the axial direction of extension of the elongated member as represented by the axis). Accordingly, elongated members 60, 70 are capable of withstanding radially-directed compression forces imposed by any and/or all of the attachment members, either during the process of implanting the elongated member along the spine (e.g., in response to clamping forces imposed by any attachment member on the elongated member) or during in situ use of the spinal stabilization system (the details of such use being described more fully hereinafter). In accordance with at least some embodiments of the present disclosure, the material and structural aspects of the elongated members 60, 70 described herein render the elongated members 60, 70 substantially rigid in axial tension, as well as substantially incompressible when subjected to axially-directed compression forces.

However, the elongated members 60, 70 of the present disclosure differ from conventional spinal stabilization rods in that the elongated members 60, 70 include enlarged heads 62, 72 at one end for placement in sockets 34, 35 of intermediate multi-level connector 30, thereby creating a dynamic junction. The elongated members 60, 70 thus retain some rotational degrees of freedom which allows for both intraoperative manipulation and angular alignment in the direction of the spine, and allows for rotational freedom post-operatively. Further, the intermediate multi-level connectors 30a, 30b generally include a second attachment member 40 for dynamic engagement with a pedicle screw 218, and a third attachment member 44 for reception of a rod at a different angular orientation to that of elongated members 60, 70. Of note, exemplary embodiments of the present disclosure effectively provide four distinct dynamic junctions across two levels.

Figures 15, 16:
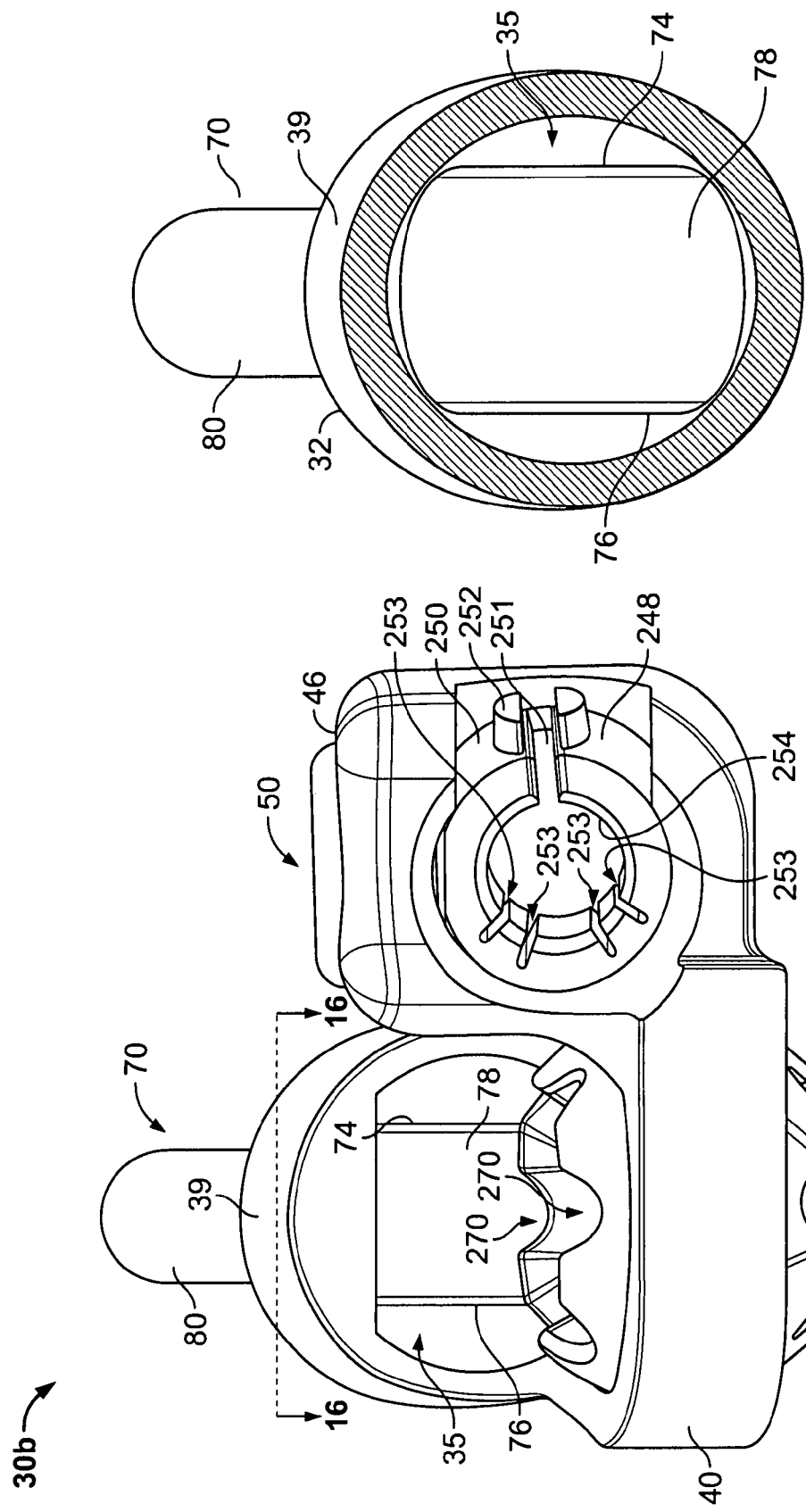
FIG. 15 is side elevational view of an intermediate multi-level connector in accordance with a further embodiment of the present disclosure.
FIG. 16 is a cross-sectional view of a socket of the intermediate multi-level connector in accordance with a second embodiment of the present disclosure engaged with an elongated member.
Figure 17:
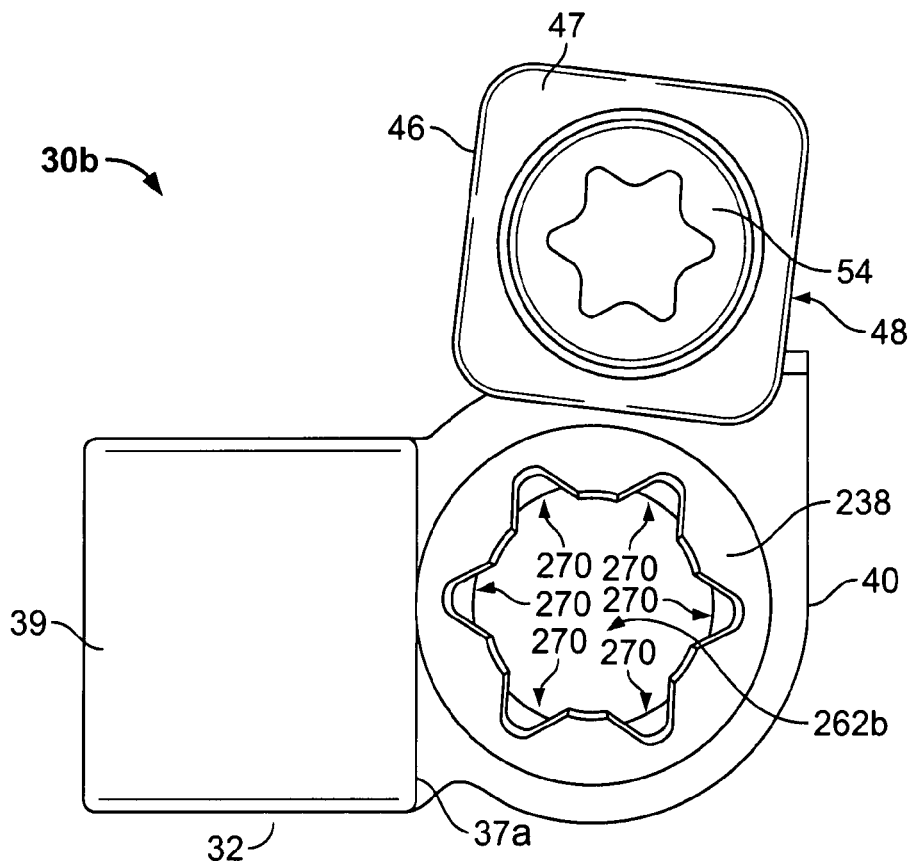
FIG. 17 is a top view of an intermediate multi-level connector in accordance with a second embodiment of the present disclosure.
Figure 18:
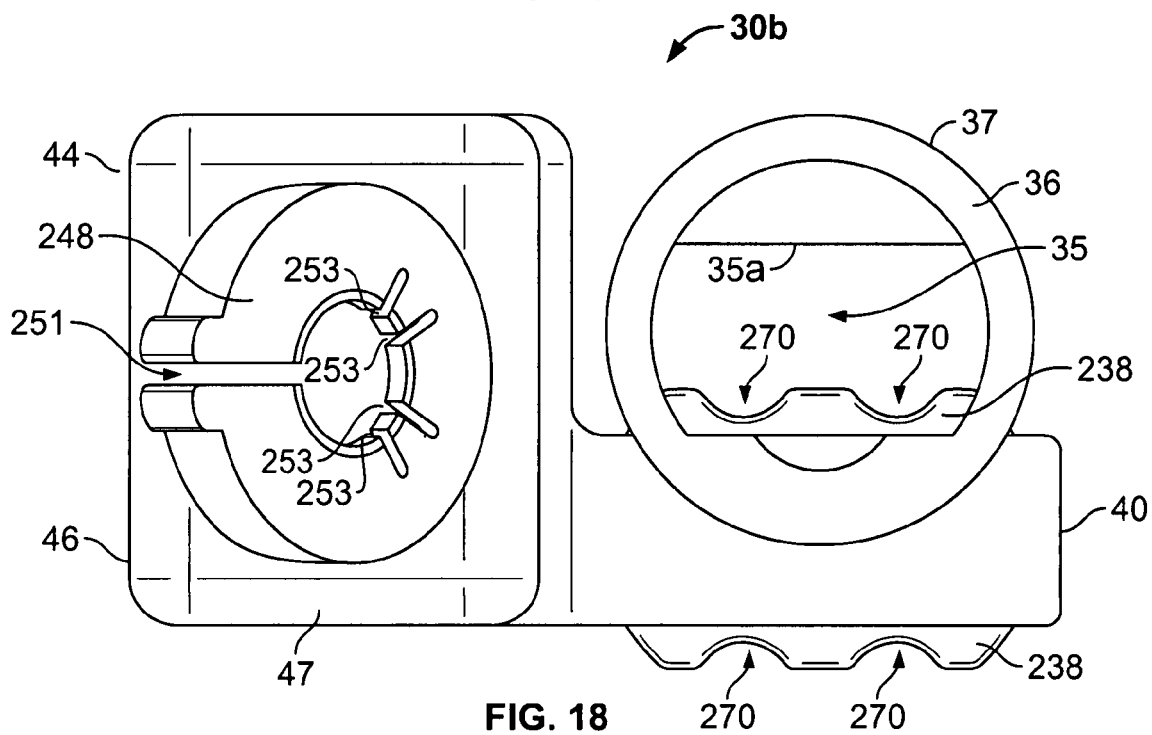
FIG. 18 is a front elevational view of an intermediate multi-level connector in accordance with a second embodiment of the present disclosure.

Referring to FIGS. 11 and 15, intermediate connectors 30a, 30b include a second attachment member 40 with a rotating ball joint, perpendicular to the axial plane of the elongated member 60, 70 in the first attachment member 32, and laterally positioned relative thereto, to receive a spherical element 238. Attachment member 40 includes a socket 42 that accommodates relative movement between the intermediate multi-level connector 30a, 30b and a pedicle screw 218. The socket 42 passes through the intermediate multi-level connector 30a, 30b such that the spherical element 238, when engaged therein, is exposed both above and below the socket 42. The dynamic junction thus formed advantageously provides three rotational degrees of freedom with respect to the pedicle screw 218. Assembly of the ball/spherical element 238 is achieved by rotating the spherical element 238 by 90 degrees relative to socket 42. At this position, the ball/spherical element 238 can slide through two opposed slots (not shown) cut in the internal spherical race of the socket 42. The socket 42 is generally aligned in a substantially perpendicular orientation relative to first socket 34 of intermediate multi-level connector 30a, 30b.

The intermediate multi-level connector 30a, 30b generally includes a third attachment member 44, unitarily formed in the body 31, that further defines a third aperture 48. The third aperture 48 passes through a substantially box-shaped housing 46, laterally positioned relative to pedicle screw socket 42. An axis passing through this third aperture 48 is substantially parallel to the axial direction of the first elongated member attached at the first socket. The aperture 48 is cylindrical in cross-section and forms/defines a socket. The box-shaped housing 46 defines an outer surface 47 that includes a bore 50 for reception of a set screw 52.

Figure 25:
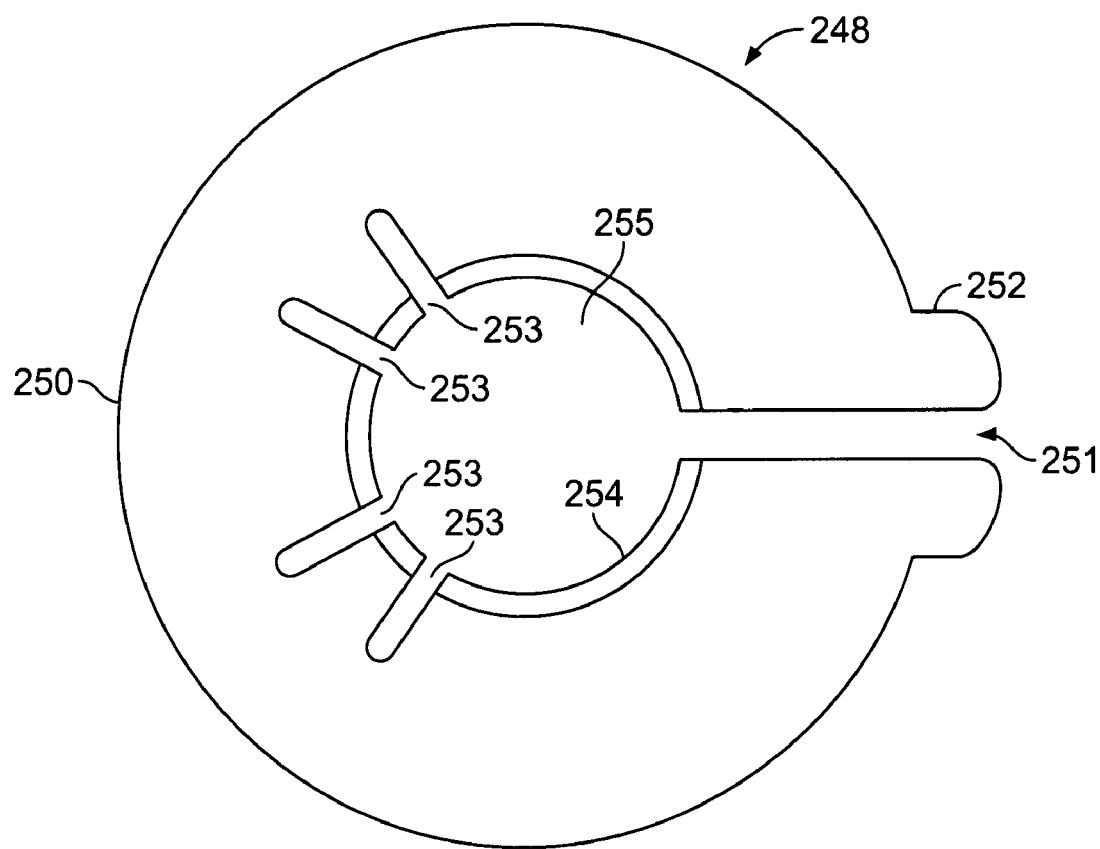
FIG. 25 is a side view of a locking ball.
Figure 26:
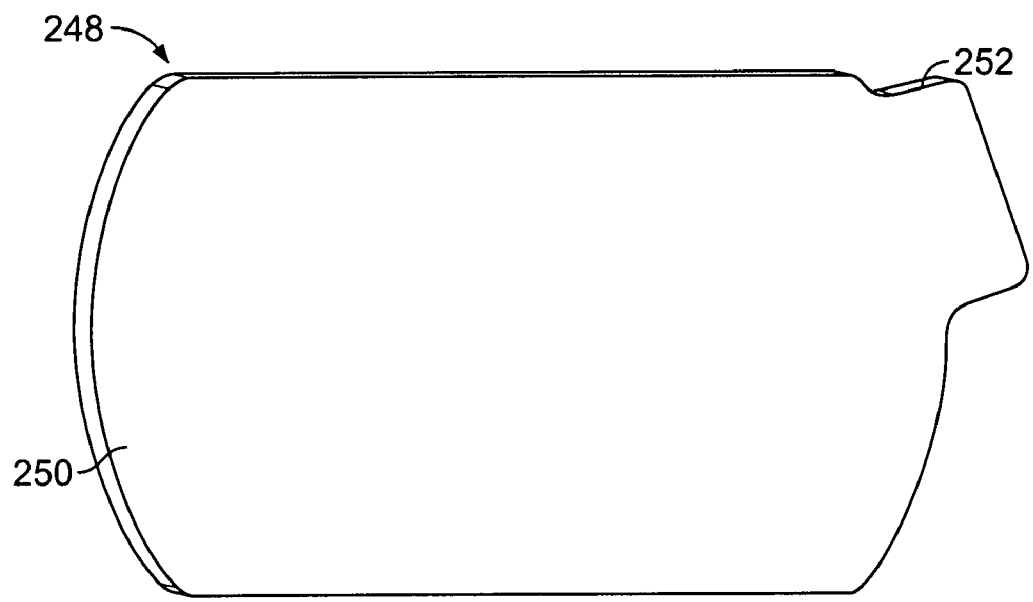
FIG. 26 is a top view of a locking ball.
Figure 27:
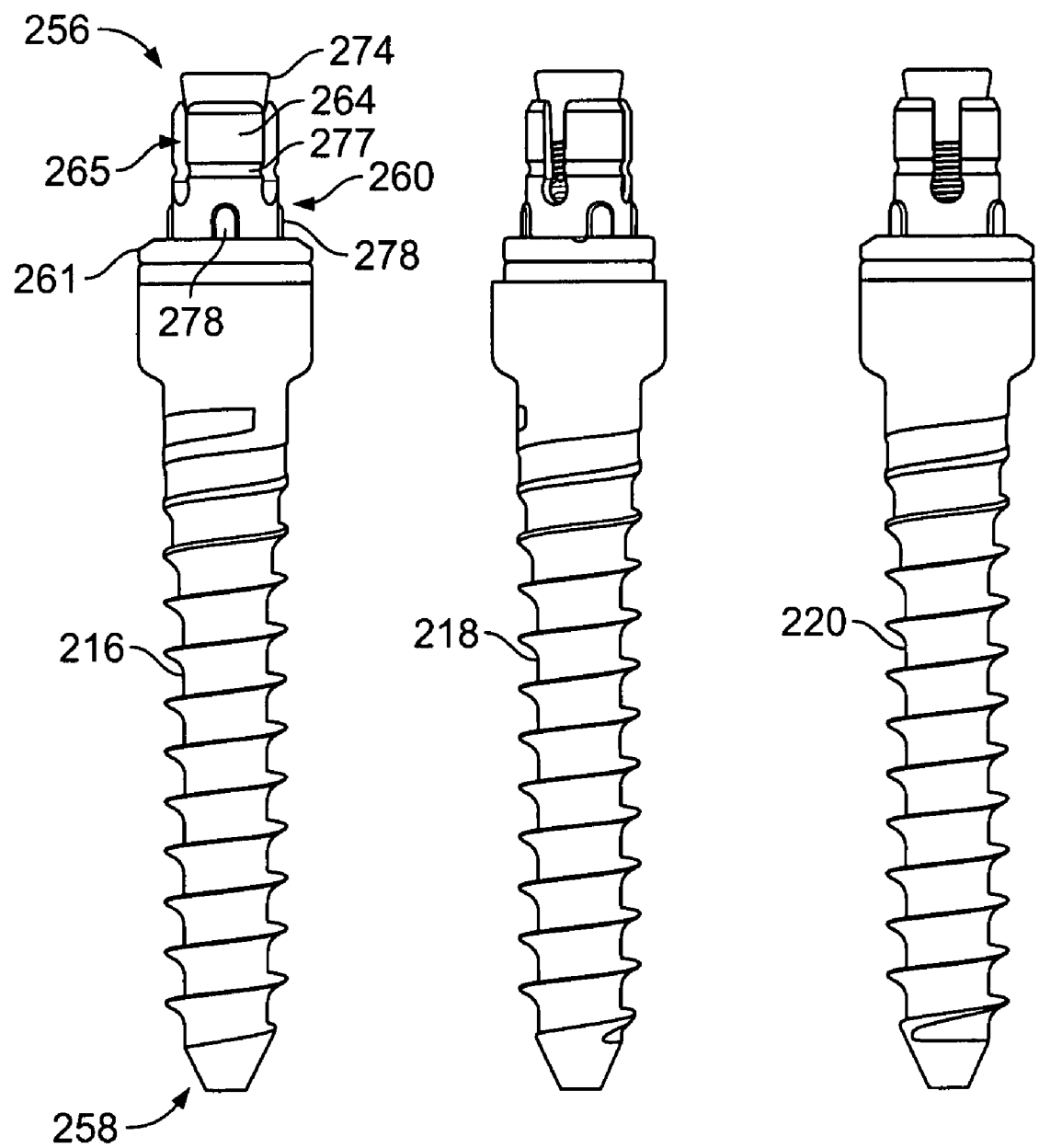
FIG. 27 is a side view of three pedicle screws with pre-loaded set screws.
Figure 28:
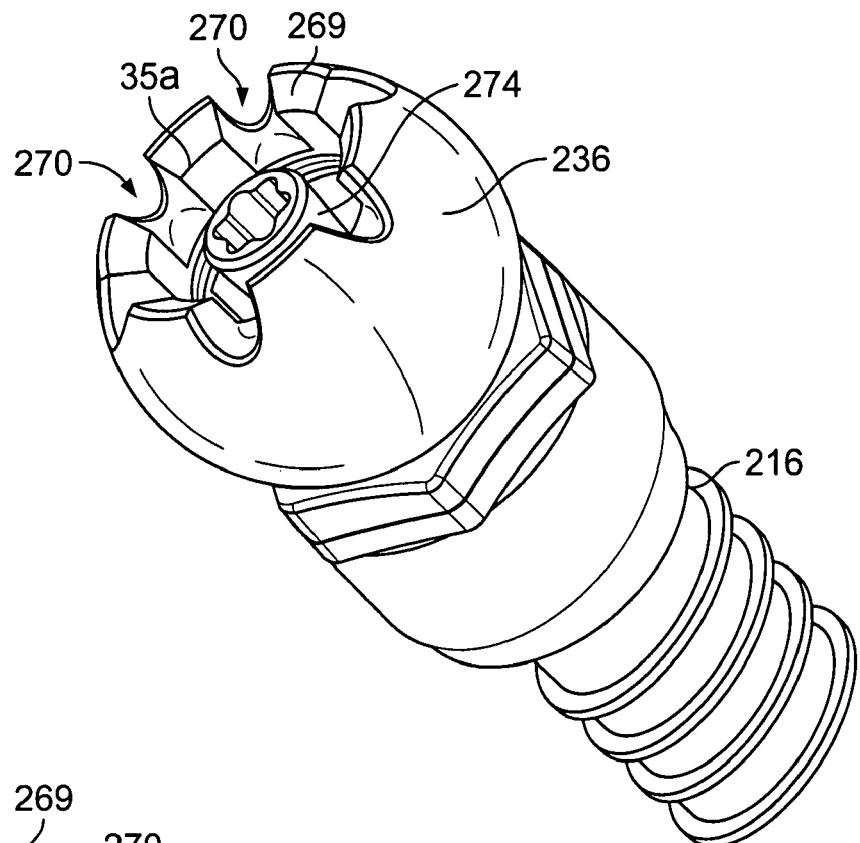
FIG. 28 is a side perspective view of a pedicle screw with a spherical element attached.

Referring to FIGS. 25 and 26, a locking ball 248 is configured and dimensioned for placement within the socket 48 of the box housing 46, forming a "ball in a box". The rotatable locking ball 248 includes a transverse compression slot 251 extending therethrough. A plurality of internal grooves 253 are also formed in the rotatable locking ball 248 to further facilitate gripping of a rod 114, 122 positioned therewithin. Bosses 252 are formed on the outside surface 250 at the compression slot 251. These bosses 252 function to keep the locking ball oriented in the socket 48 so that the compression slot 251 is always rotated away from the axis of the set screw 52. Such relative alignment ensures that, when tightening the set screw 52, the locking ball remains in an orientation that allows the compression slot 251 to compress the rod 114, 122 that passes through its aperture 255. Without such bosses 252, the compression slot 251 could rotate in line with the axis of the se screw 52 resulting in an opening of the locking ball 248 and no tightening of the rod 114, 122.

The rod 114, 122 passes through the aperture 255 of the locking ball 248 in the third attachment member 44 of the intermediate multi-level connector 30a, 30b, and extends axially down the spine, away from the intermediate multi-level connector 30a, 30b toward the first, inferior end 20 of the multi-level spinal stabilization system. The rod 114, 122 is fixed by means of the set screw 52 pressing on the outer surface 250 of the locking ball 248.

Referring to FIGS. 20-24, at the first end 20 of the system 10, the dynamic stabilization system provides an inferior vertebral connector 100, 120. In one embodiment, inferior vertebral connector 100 receives the rod of a straight elongated member 114 in an attachment member 102 through an aperture 106 of a ball-in-a-box housing 104 with a locking ball 248 similar to that of the intermediate multi-level connector 44 described above. The ball-in-a-box housing 104 of the inferior vertebral connector 100 also includes a threaded bore 110 extending from an internal socket to an outer surface 108 of the box-shaped housing for reception of a set screw 52. The inferior vertebral connector 100 is selectively positioned at an angle with respect to the spinal axis and the intermediate multi-level connector 30 to accommodate individual patient anatomy. When positioned at a desired axial orientation, the rod 114 is statically fixed by means of the set screw 52.

The first embodiment of the inferior vertebral connector 100 includes a second attachment member 103 for reception of a spherical element 240 fixed to a pedicle screw 216. The spherical element 236 passes through a socket 112 and accommodates movement of the inferior vertebral connector 100 relative to the pedicle screw 220, advantageously providing three rotational degrees of freedom.

Figure 21B:
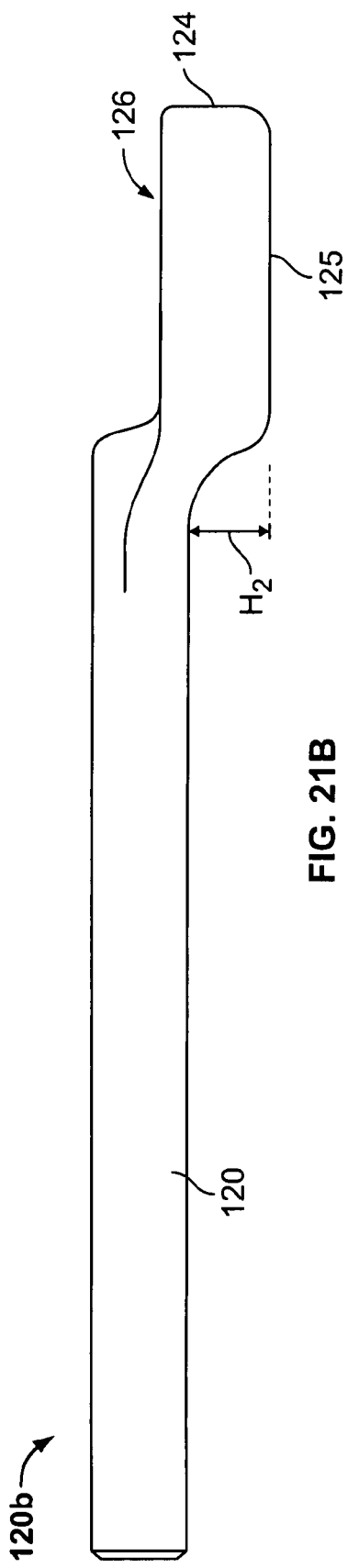
FIG. 21b is a side elevational view of a first embodiment of an inferior vertebral connector, a rod on a ring showing a high rod to ring offset.
Figure 21C:
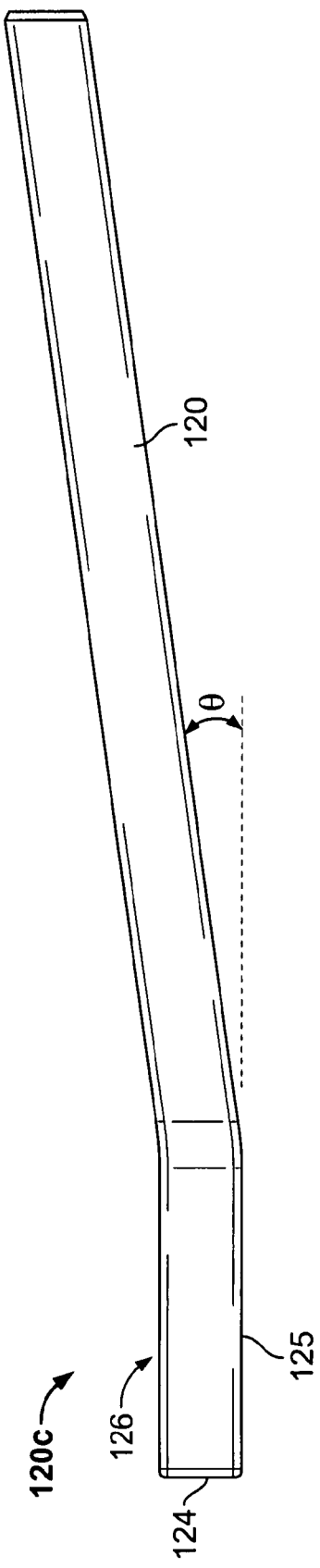
FIG. 21c is a side elevational view of a first embodiment of an inferior vertebral connector, a rod on a ring showing an angled rod to ring configuration.
Figure 22:
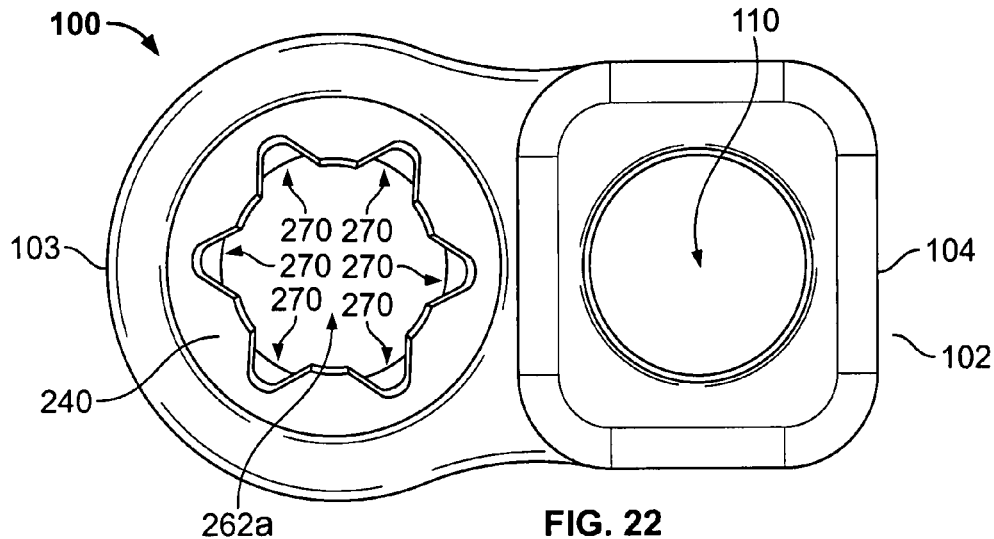
FIG. 22 is a top view of a second embodiment of an inferior vertebral connector, a ball in a box.
Figure 23:
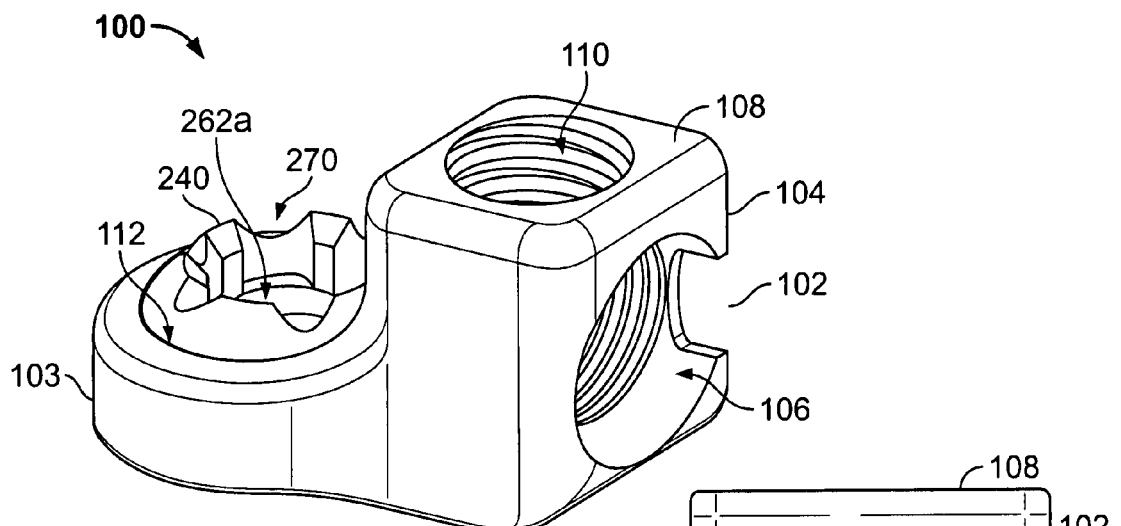
FIG. 23 is a right side perspective view of a second embodiment of an inferior vertebra connector, a ball in a box.
Figure 24:
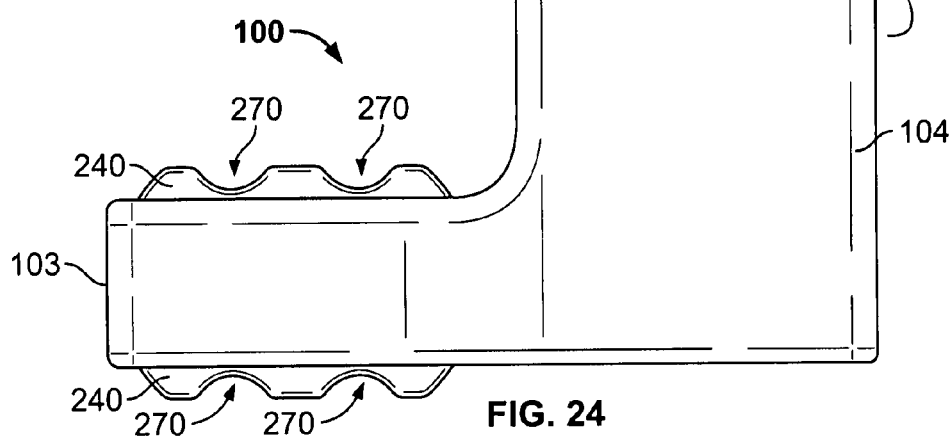
FIG. 24 is a back elevational view of a second embodiment of an inferior vertebral, a ball in a box.

Referring to FIGS. 20-21a-c, additional exemplary embodiments of an inferior vertebral connector 120 are depicted. Connectors 120 include a rod 122 with a ring 124 formed or positioned at a distal end 128 thereof. The ring 124 defines a socket 126 configured and dimensioned for reception of a spherical element 240 for fixation of or cooperation with a pedicle screw 220. In these exemplary embodiments, the socket 126 of the inferior connector 120 is typically unitarily formed with a rod 122 which extends axially toward the intermediate, multi-level connector 30a, 30b. A first embodiment of the rod and ring connector 120a is dimensioned and configured such that the rod 122 extends parallel to the bottom surface 125 of the ring 124 with a low offset $H_1$. In a second embodiment 120b, the rod 122 extends parallel to bottom surface 125 of the ring 124 at a higher offset $H_2$. In a third embodiment, the rod 122 extends from the ring at angle "θ", such that the rod 122 does not extend parallel to the bottom surface of the ring 124.

The inferior vertebral connector of any of exemplary embodiments 100, 120a-c provides superior stabilization by virtue of, inter alia, its relatively small geometry and ability to be advantageously oriented with respect to the spine and the disclosed intermediate connector to accommodate varying patient anatomies. For example, at the sacrum, the physical space between the first sacral vertebra and the last lumbar vertebra is narrowly limited by the pelvic anatomy. The stabilization members 100, 120a-c at the first end 20 of the stabilization system 10 of the various embodiments herein, are advantageously dimensioned and configured to fit in the confined, narrow region between the wings of the first sacral vertebra "S" and lumbar vertebra/pedicles "P" in a desired orientation for connection to the intermediate multi-level connector 30. However, it should be noted that the inferior vertebral connectors 100, 120a-c are not limited to use in the lumbo-sacral junction.

The multi-level system of the first embodiment 10 has a second end 22 located two levels above the inferior vertebral connector that includes a third connector 130 that is dimensioned and configured with a "ball-in-a-box" housing 132 and a locking ball 248 for reception of a rod 68, 80 of elongated element 60,70. The third connector 130 includes a second attachment member 136 to receive spherical element 236 of a pedicle screw 216 to accommodate relative movement between the third connector 130 and a pedicle screw 216, where the spherical element 240 is mounted with respect to the pedicle screw 216.

Referring to FIGS. 27-30, an exemplary multi-level spinal stabilization system according to the present disclosure is shown in combination with pedicle screws 216, 218, 220. Each of the pedicle screws 216, 218, 220 includes a proximal end 256 and a distal end 258 (inasmuch as the first, second and third pedicle screws 216, 218, 220, respectively, in the exemplary embodiment depicted herein are identical, the same numeric designations will be used in describing all pedicle screws; however, it is contemplated that pedicle screws having differing structural and/or functional features may be incorporated into spinal stabilization system implementations according to the present disclosure without departing from the spirit or scope hereof).

The distal end 258 includes conventional threading adapted for secure attachment along the spinal column of an individual. According to exemplary embodiments of the present disclosure and with further reference to FIG. 27, each of the proximal ends 256 of the pedicle screws 216, 218, 220 is provided with a collet 260 that is sized for receipt within ball/spherical element 236. Collet 260 is fabricated and/or formed with an ability to expand and contract, e.g., under the control of medical practitioner(s) involved in using spinal stabilization system 10. Exemplary collet 260 includes a plurality of upstanding segments 264 that are arranged in a substantially arcuate manner around a central cavity 266, i.e., around the periphery of central cavity 266. Adjacent upstanding segments 264 are separated by a slot or channel 265. Nubs 278 are integrally formed for engagement with corresponding geometry of the spherical element 236

According to exemplary embodiments of the present disclosure, the receiving channel 262 of the respective spherical element 236 is configured and dimensioned for receiving a collet 260 associated with a pedicle screw 216 while in its unexpanded (or substantially unexpanded) state (inasmuch as the first, second and third pedicle screws 236, 238, 240 in the exemplary embodiment depicted herein are identical, the same numeric designations will be used in describing all spherical elements; however, it is contemplated that spherical elements having differing structural and/or functional features may be incorporated into stabilizing system implementations according to the present disclosure without departing from the spirit or scope hereof).

The receiving channel 262 generally includes first and second chamfered regions at opposite ends thereof (not shown). The chamfered regions facilitate alignment and connection of components of the disclosed spinal stabilization system 10, e.g., interaction between pedicle screws 216 and balls/spherical elements 236. To facilitate flexibility in use of the disclosed spinal stabilization system 10, balls/spherical elements 236 are generally symmetric around or relative to a mid-plane. Accordingly, the chamfered regions at either end of receiving channels 262 are substantially identical in geometry and dimension.

According to exemplary embodiments of the present disclosure, structural features and/or elements 270 are provided on ball/spherical element 236 and/or collet 260 to facilitate interaction with one or more tools, e.g., tools for securing a ball/spherical element relative to a pedicle screw 216, and/or other components associated with spinal stabilization system 10. The tabs/cut-out features 270 shown in FIGS. 29-30 include a substantially U-shaped geometry, although alternative geometries may be employed to accommodate specific tool designs and/or tool interactions. In the exemplary embodiments of FIGS. 29-30, a tool (not pictured) may advantageously interact with adjacent alignment tabs/cut-outs 270, e.g., through arcuately arranged gripping extensions that are spaced, configured and dimensioned to engage/cooperate with adjacent alignment tabs/cut-outs 270. The disclosed alignment tabs/cut-outs 270 are typically formed at both ends of balls/spherical elements 236, 238, 240. Indeed, the provision of alignment tabs/cut-outs 270 on both ends of balls/spherical elements 236, 238, 240 advantageously facilitates the mounting of a ball 236, 238, 240 in either orientation without sacrificing functionality/interactivity, e.g., interaction with an ancillary tool or the like.

Figure 29:
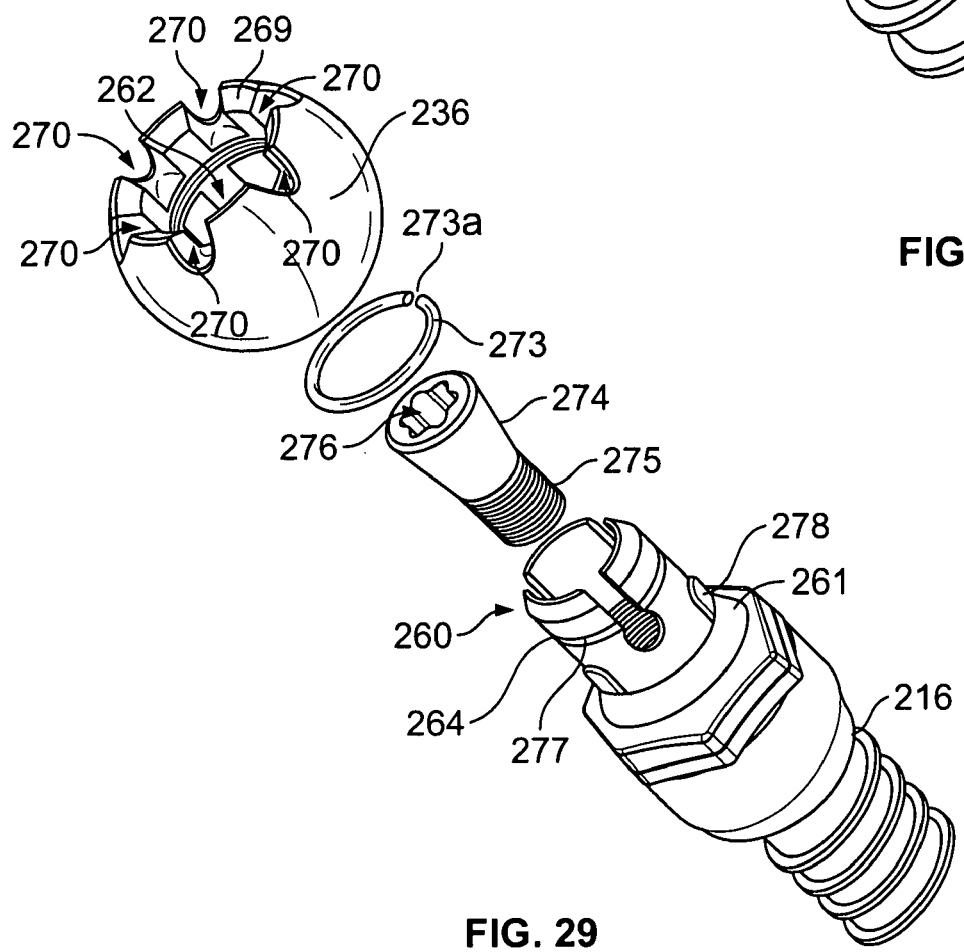
FIG. 29 is a side exploded view of a pedicle screw subassembly.
Figure 30:
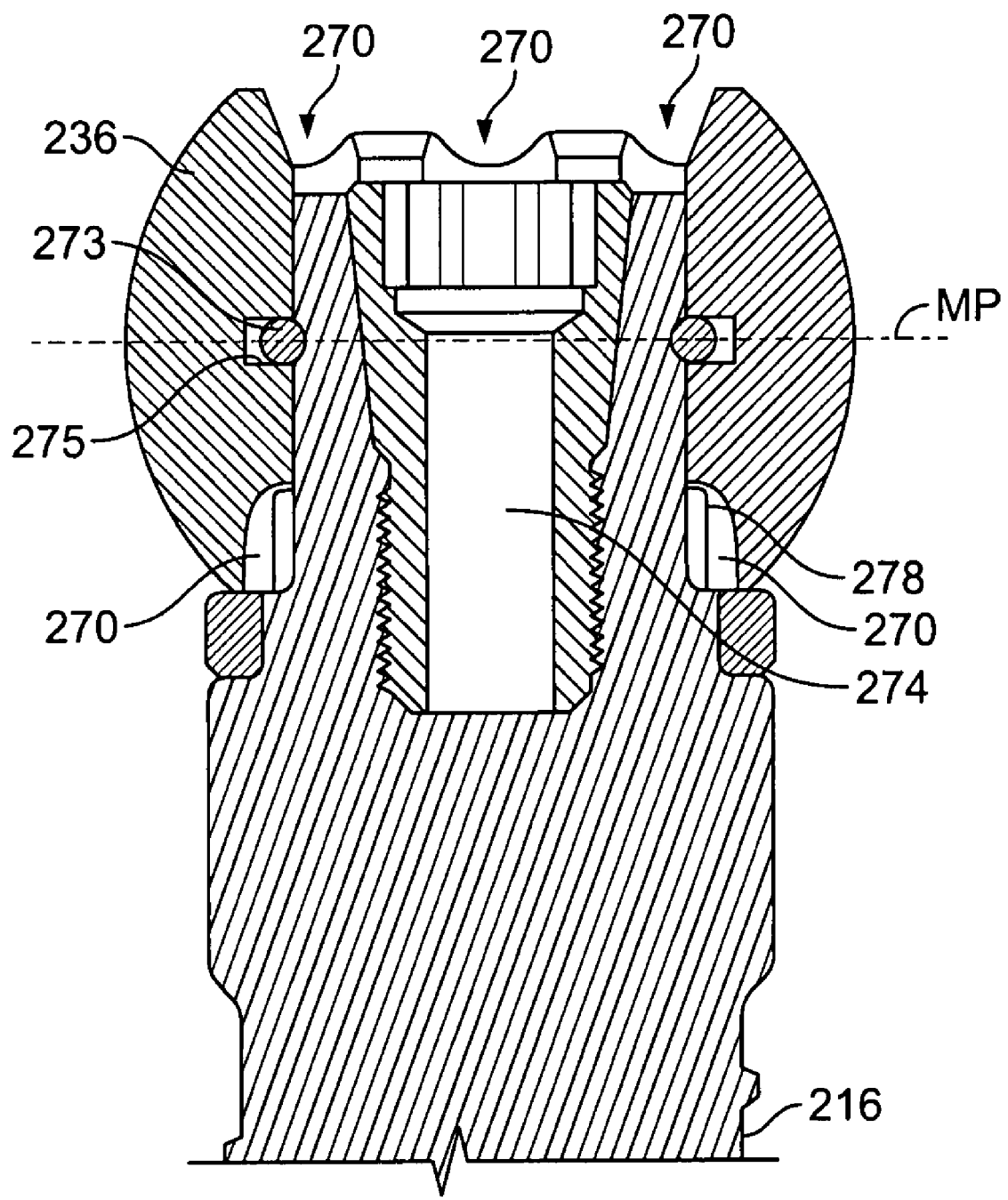
FIG. 30 is a cross-sectional view of a pedicle screw with spherical element attached.

With reference to FIG. 29, a collet-based system for securing or mounting a ball/spherical element 236 relative to a pedicle screw 216 according to the present disclosure is depicted. Nubs 278 are integrally formed at the base of the collet 260. Nubs 278 define a substantially hemispherical first end for cooperation with the tabs/cut-outs 270 of the spherical element 236 for locking the spherical element 236 in place with respect to the collet 260.

An internal snap ring 273 is also generally provided that is configured to cooperate with an external ring groove 277 formed in the outer wall of upstanding segments 264 and an internal ring groove (not pictured) formed in ball/sphere 236. Snap ring 273 defines a partial circle, with opening 273a facilitating expansion of the diameter of snap ring. Typically, snap ring 273 is fabricated from an appropriate metallic material, e.g., titanium or stainless steel, that provides a desired degree of elasticity. The depths of external 277 and internal ring grooves, respectively, are generally selected to ensure seating of snap ring 273.

In use, snap ring 273 is typically positioned in the internal groove formed in the ball/spherical element 236 and essentially "snaps" into place with the outer groove 277 formed in the collet 260, i.e., when the components reach the desired alignment. This "snap" connection between the ball/spherical element 236 and the collet 260/pedicle screw 216 allows the clinician to take appropriate steps to more permanently secure the components relative to each other (e.g., to locate and position appropriate tools) without risk that the components will become misaligned. Thus, the snap ring 273 advantageously aligns with and partially nests within both ring grooves thereby providing a further engagement between ball/sphere 236. As set screw 274 is screwed into place, the upstanding segments 264 deflect outward, thereby providing a greater engagement between ball/sphere 236 and pedicle screw 216. In alternative embodiments hereof, the snap ring 273 may be initially positioned on the outer surface of the collet 260 (i.e., in the outer groove 277), in which case the snap ring 273 "snaps" into the inner groove 275 of the ball/spherical 236 alignment when the desired alignment is achieved.

When the spine moves in flexion, pedicle screws are subject to forces that bias the pedicle screws away from each other. The forces experienced by pedicle screws as the spine moves in flexion are translated to first, second and third attachment members, which similarly experience a force that biases such components of the spinal stabilizing system away from each other. Once the pedicle screws are properly installed, the distance between the pedicle screws is generally measured and the rod may be cut to proper dimension, or placed within the attachment members, as appropriate. Alternatively, elongated members that feature varying length rods may be provided to permit a clinician to select a rod of desired length.

At this stage of assembly/installation, the spherical elements 236, 238, 240 are secured relative to the corresponding collet 260 of the corresponding pedicle screws 216, 218, 220. However, according to the present disclosure, dynamic junctions are nonetheless established because the connectors are free to move, e.g., rotate, relative to the spherical elements 236, 238, 240. As such, realignment and/or reorientation of each of the connectors is possible so as to facilitate alignment with an adjacent pedicle screw 216, 218, 220, i.e., for assembly of a dynamic stabilization level. Of particular note, even after mounting of a connector relative to an adjacent pedicle screw, the dynamic junction remains operative at the initial pedicle screw described herein, thereby accommodating anatomical shifts that may arise after installation of the disclosed dynamic stabilization system.

In general, tightening and/or locking of a spherical element 236, 238, 240 relative to a pedicle screw 216, 218, 220 is thus undertaken according to exemplary embodiments of the present disclosure by threading a set screw 274 into a central aperture positioned at or near the head of the pedicle screw. The set screw 274 may be advantageously pre-loaded into the central aperture to facilitate clinical use thereof. Threading of the set screw 274 into the central aperture causes an outward deflection of a series of upstanding elements 264 associated with a collet mechanism 260 associated with the pedicle screw 216, 218, 220. To facilitate movement of the set screw 274 relative to the pedicle screw 216, 218, 220, it is generally desirable to impart a "counter-torque" force to the pedicle screw 216, 218, 220 so as to prevent/limit rotational motion of the pedicle screw 216, 218, 220 as the set screw 274 is inserted or withdrawn relative to the central aperture. Tools for providing a desired counter-torque (and for inserting/withdrawing a set screw) are known.

With further reference to FIGS. 1-30, at the disclosed intermediate connector, the enlarged head 64, 72 of the elongated member 60, 70 is positioned in the rotating socket 35 in the cylindrical housing 36 and remains free to rotate relative to the intermediate multi-level connector 30a, 30b. Realignment and/or reorientation of the longitudinal rod portion 68, 80 of the elongated member 60, 70 is possible with respect to the third connector 130 at the second end 22, and the enlarged head 64, 72 remains dynamic for movement to accommodate anatomical shifts after installation. As with pedicle screws 216, 218, 220, a dynamic junction is advantageously defined between socket 35 and the enlarged head 64, 72 of elongated member 60, 70. The elongated member 60, 70 extends axially from the socket 35 to the third connector 130 at the second end 22 of the disclosed spinal stabilization system. The elongate member 60, 70 becomes locked in place after passing through the aperture in the box-shaped housing 132 by virtue of a set screw 52 tightened at the transverse aperture.

At the first end, the inferior vertebral connector 100, 120 is intra-operatively aligned with respect to the intermediate connector 30 so that the longitudinal rod member 68, 122 extending therefrom passes through the aperture 48 of the third attachment member 44 of the intermediate connector 30 at a desired angular orientation. Once in place, a set screw 52 is threaded through the transverse aperture 50 of the intermediate connector 30 to lock the elongated member 68, 122 in position. In a second exemplary embodiment of the inferior vertebral connector 100, a set screw 54 is likewise threaded through the transverse aperture 110 of the box-shaped housing 104 to lock the rod 114 in position. As with installation of the pedicle screws 216, 218, 220, the set screw 54 of the inferior vertebral connector can be pre-loaded to facilitate clinical use thereof. The installation procedure is generally repeated on the opposite side of the vertebrae to complete at least two levels of dynamic stabilization using three pedicle screws.

Stabilization of the load at the intermediate multi-level connector 30a, 30b occurs only after locking elongated members at the adjoining levels that are inferior and superior to the intermediate multi-level connector 30a, 30b at the "ball in a box" construct(s). Stress is relieved at the interface between the pedicle bones and the pedicle screws due to the rotating spherical element/socket dynamic connections, where the centers of the rotating spheres are offset in two planes.

As noted above, the embodiments disclosed herein are merely illustrative of the disclosed spinal stabilization devices, systems and surgical implants, and the methods/techniques for implementation thereof. Such spinal stabilization devices, systems, surgical implants and methods/techniques may be changed, modified, varied and/or enhanced without departing from the spirit or scope of the present disclosure. Accordingly, the present disclosure expressly encompasses such changes, modifications, variations and/or enhancements within its scope.

What is claimed is:

1. A connection assembly for a spinal stabilization system, comprising:
   (a) an elongated member having a central longitudinal axis and defining an enlarged head at one end thereof, the elongated member extending from said enlarged head defining an elongated portion having an outer perimeter smaller than the outer perimeter of said enlarged head;
   (b) a connection member defining at least one socket that is configured and dimensioned to receive and capture said enlarged head of said elongated member, the at least one socket including a first opening and a second opening in communication with the first opening;
   the first opening extending through the outer top surface of said at least one socket to the second opening, the first opening configured and dimensioned to: (i) receive said elongated portion of said elongated member, and (ii) not be able to receive said enlarged head;
   the second opening configured and dimensioned to receive said enlarged head substantially simultaneously with said first opening receiving said elongated portion;
   wherein said enlarged head is captured by said at least one socket by rotating the elongated portion out of said first opening, said at least one socket preventing said enlarged head from exiting said at least one socket when said elongated portion is out of said first opening; and
   wherein the elongated member is free to rotate about the central longitudinal axis when captured by the at least one socket.

2. The connection assembly of claim 1, wherein said elongated portion is a rod.

3. The connection assembly of claim 1, wherein said enlarged head defines a substantially spherical geometry.

4. The connection assembly of claim 1, wherein said enlarged head defines a substantially disk-like geometry.

5. The connection assembly of claim 1, wherein said enlarged head is unitarily formed with the elongated portion.

6. The connection assembly of claim 1, wherein said first opening is a slot.

7. The connection assembly of claim 6, wherein said slot is U-shaped.

8. The connection assembly of claim 1, wherein said enlarged head of said elongated member is free to move relative to said socket when captured by and while remaining engaged therewith.

9. The connection assembly of claim 1, further comprising an attachment member for mounting with respect to a pedicle screw.

10. The connector assembly of claim 9, further comprising a further attachment member that defines a rod-receiving opening that is laterally positioned relative to said socket.

11. The connector assembly of claim 10, wherein said second opening and said rod-receiving opening define axes that are substantially parallel.

12. A multi-level spinal stabilization system, comprising:
   (a) a first connector that defines a dynamic junction and that is dynamically mounted with respect to a first pedicle screw;
   (b) a second connector that defines a second dynamic junction and that is dynamically mounted with respect to a second pedicle screw;
   (c) an intermediate connector that defines a third dynamic junction and that is dynamically mounted with respect to a third pedicle screw, said third pedicle screw being positioned between said first pedicle screw and said second pedicle screw;
   (d) a first elongated member extending between and mounted with respect to said first connector and said intermediate connector, said first elongated member having a central longitudinal axis and defining an enlarged head at one end thereof, said first elongated member extending from said enlarged head defining an elongated portion having an outer perimeter smaller than the outer perimeter of the enlarged head;
   (e) a second elongated member extending between and mounted with respect to said second connector and said intermediate connector;
   wherein said intermediate connector defines a socket and a rod-receiving opening laterally spaced from said socket, said socket configured and dimensioned to receive and capture said enlarged head of said first elongated member, said socket including a first opening and a second opening in communication with said first opening, said first opening configured and dimensioned to: (i) extend through the outer surface of the socket to the second opening, (ii) receive said elongated portion of said first elongated member, and (iii) not be able to receive said enlarged head of said first elongated member;
   wherein the second opening of said socket is configured and dimensioned to receive said enlarged head substantially simultaneously with said first opening receiving said elongated portion;
   wherein said first elongated member is dynamically mounted with respect to said socket of said intermediate connector by rotating said elongated portion of said first elongated member out of the first opening thereby capturing said enlarged head of said first elongated member in said socket, said socket preventing said enlarged head from exiting said socket when said elongated portion is out of the first opening;

wherein the first elongated member is free to rotate about the central longitudinal axis when captured by the socket of the intermediate connector; and wherein said second elongated member is non-dynamically mounted with respect to said rod-receiving opening.

13. The multi-level spinal stabilization system of claim 12, wherein said second elongated member is integrally formed with said second connector.

14. The multi-level spinal stabilization system of claim 12, wherein said elongated portion is a rod.

15. The multi-level spinal stabilization system of claim 14, wherein said enlarged head defines a substantially spherical geometry.

16. The multi-level spinal stabilization system of claim 14, wherein said enlarged head defines a substantially disc-like geometry.

17. The multi-level spinal stabilization system of claim 14, wherein said enlarged head is unitarily formed with the elongated portion.

18. The multi-level spinal stabilization system of claim 17, wherein said first opening is a slot.

19. The multi-level spinal stabilization system of claim 18, wherein said slot is U-shaped.

20. The multi-level spinal stabilization system of claim 19, wherein said enlarged head of said elongated member is free to move relative to said socket when captured by and while remaining engaged therewith.

* * * * *